US011619236B2

(12) United States Patent
Schöb et al.

(10) Patent No.: US 11,619,236 B2
(45) Date of Patent: Apr. 4, 2023

(54) PUMPING DEVICE, A SINGLE-USE DEVICE AND A METHOD FOR OPERATING A PUMPING DEVICE

(71) Applicant: Levitronix GmbH, Zürich (CH)

(72) Inventors: Reto Schöb, Wollerau (CH); Natale Barletta, Zürich (CH)

(73) Assignee: LEVITRONIX GMBH, Zürich (CH)

( * ) Notice: Subject to any disclaimer, the term of this patent is extended or adjusted under 35 U.S.C. 154(b) by 101 days.

(21) Appl. No.: 17/147,846

(22) Filed: Jan. 13, 2021

(65) Prior Publication Data
US 2021/0254623 A1    Aug. 19, 2021

(30) Foreign Application Priority Data
Feb. 13, 2020   (EP) ..................... 20157146

(51) Int. Cl.
*F04D 13/14*    (2006.01)
*F04D 13/06*    (2006.01)
(Continued)

(52) U.S. Cl.
CPC ............. *F04D 13/024* (2013.01); *F04D 1/06* (2013.01); *F04D 13/027* (2013.01);
(Continued)

(58) Field of Classification Search
CPC ........ F04D 13/024; F04D 1/06; F04D 13/027; F04D 13/0626; F04D 13/064;
(Continued)

(56) References Cited

U.S. PATENT DOCUMENTS 5,405,251 A * 4/1995 Sipin .................... F04D 29/043
417/423.1
5,855,782 A * 1/1999 Falkenhagen ....... A61M 1/3472
210/201

(Continued)

FOREIGN PATENT DOCUMENTS

| WO | 96/31934 A1 | 10/1996 | |
|---|---|---|---|
| WO | 98/11650 A1 | 3/1998 | |
| WO | WO-2004098677 A1 * | 11/2004 | .......... A61M 1/1015 |

OTHER PUBLICATIONS

Lorforte et al., "Levitronix CentriMag Third-Generation Magnetically Levitated Continuous Flow Pump as Bridge to Solution", ASAIO Journal: Jul. 2011—vol. 57—Issue 4—p. 247-253 (Year: 2011).*

(Continued)

*Primary Examiner* — Dominick L Plakkoottam
(74) *Attorney, Agent, or Firm* — Global IP Counselors, LLP

(57) ABSTRACT

A pumping device includes a single-use device and a reusable device. The single-use device is to be inserted into the reusable device and includes two pump units in series, one behind the other. Each pump unit includes a rotor for a bearingless motor, and can be magnetically levitated and driven without contact for rotation about an axial direction. The reusable device includes a stator for each rotor which form an electromagnetic rotary drive for rotating the rotor about the axial direction. Each stator is a bearing and drive stator with which the rotor can be magnetically driven and levitated without contact with respect to the stator. An independent control device is provided for each stator, and can independently activate a respective stator.

15 Claims, 13 Drawing Sheets

(51) Int. Cl.
  *F04D 13/02* (2006.01)
  *F04D 29/18* (2006.01)
  *F04D 1/06* (2006.01)
  *A61M 60/232* (2021.01)
(52) U.S. Cl.
  CPC ....... *F04D 13/064* (2013.01); *F04D 13/0626* (2013.01); *F04D 13/0686* (2013.01); *F04D 13/14* (2013.01); *F04D 29/186* (2013.01); *A61M 60/232* (2021.01)
(58) Field of Classification Search
  CPC .... F04D 13/0686; F04D 13/14; F04D 29/186; F04D 13/0606; F04D 29/628; F04D 29/048; F04D 13/0666; F04D 29/426; F04D 13/06; F04D 15/0066; F04D 15/0072; A61M 60/232; A61M 60/113; A61M 60/226; A61M 60/38; A61M 60/422; A61M 60/538; A61M 60/845; A61M 60/849; A61M 2205/17; F16C 41/008; F16C 32/0497; H02K 2211/03; H02K 11/33; H02K 5/02; H02K 11/20; H02K 2213/03; H02K 1/276; H02K 5/128; H02K 7/09; H02K 7/14
  See application file for complete search history.

(56) References Cited

U.S. PATENT DOCUMENTS

| | | | |
|---|---|---|---|
| 6,171,078 B1 * | 1/2001 | Schob | A61M 60/824 417/423.1 |
| 8,985,969 B2 * | 3/2015 | Hoshi | F04D 13/02 417/423.15 |
| 9,044,535 B2 * | 6/2015 | Garzaniti | A61M 60/422 |
| 9,239,057 B2 * | 1/2016 | Hoshi | F04D 13/06 |
| 10,707,734 B2 * | 7/2020 | Holenstein | B01F 33/4535 |
| 10,895,262 B2 * | 1/2021 | Chen | F04D 3/00 |
| 2001/0039369 A1 * | 11/2001 | Terentiev | A61M 60/876 600/16 |
| 2010/0280305 A1 * | 11/2010 | Hidaka | A61M 60/806 600/16 |
| 2012/0156071 A1 * | 6/2012 | Hijikata | F04D 29/605 417/423.12 |
| 2013/0022481 A1 * | 1/2013 | Schob | F04D 29/048 310/156.01 |
| 2014/0271123 A1 * | 9/2014 | Rosinski | F04D 29/426 415/60 |
| 2015/0252808 A1 * | 9/2015 | Rosinski | F04D 13/06 417/423.5 |
| 2016/0338223 A1 * | 11/2016 | Tsai | F28F 3/12 |
| 2017/0040868 A1 | 2/2017 | Noh et al. | |
| 2018/0193542 A1 | 7/2018 | Desilva et al. | |
| 2019/0013747 A1 * | 1/2019 | Barletta | F04D 29/048 |
| 2019/0055946 A1 * | 2/2019 | Luxford | B01D 35/26 |
| 2021/0025399 A1 * | 1/2021 | Wu | F04D 1/06 |
| 2021/0079922 A1 * | 3/2021 | Schmid | F04D 29/048 |

OTHER PUBLICATIONS

Extended European Search Report dated Jul. 27, 2020 in corresponding European Patent Application No. 20157146.0, filed Feb. 13, 2020.

* cited by examiner

PUMPING DEVICE, A SINGLE-USE DEVICE AND A METHOD FOR OPERATING A PUMPING DEVICE

CROSS-REFERENCE TO RELATED APPLICATION

This application claims priority to European Patent Application No. 20157146.0, filed Feb. 13, 2020, the contents of which are hereby incorporated herein by reference in their entirety.

BACKGROUND

Field of the Invention

The invention relates to pumping device for conveying a fluid, to a single-use device for such a pumping device and to a method for operating a pumping device.

Background Information

In biotechnological or medical technology applications, pumps are often required with which very sensitive substances such as blood or cell cultures or proteins can be conveyed, whereby it is very important that these substances are damaged by the pump as little as possible. For this purpose, peristaltic pumps are known on the one hand and centrifugal pumps on the other hand, in which a rotating rotor (impeller) with vanes acts on the fluid to be conveyed.

Conventional centrifugal pumps are known which comprise an electromagnetic rotary drive, which is designed and operated according to the principle of the bearingless motor. In this respect, the term bearingless motor means an electromagnetic rotary drive in which the rotor is levitated completely magnetically with respect to the stator, wherein no separate magnetic bearings are provided. For this purpose, the stator is designed as a bearing and drive stator, which is both the stator of the electric drive and the stator of the magnetic levitation. A magnetic rotating field can be generated by the electrical windings of the stator, which magnetic rotating field, on the one hand, exerts a torque onto the rotor, which effects its rotation and which, on the other hand, exerts a shear force, which can be set as desired, onto the rotor so that its radial position can be actively controlled or regulated. Thus, three degrees of freedom of the rotor can be actively regulated, namely its rotation and its radial position (two degrees of freedom). With respect to three further degrees of freedom, namely its position in the axial direction and tilts with respect to the radial plane perpendicular to the desired axis of rotation (two degrees of freedom), the rotor is passively magnetically levitated or stabilized by reluctance forces, i.e. it cannot be activated. The absence of a separate magnetic bearing with a complete magnetic levitation of the rotor is the property, which gives the bearingless motor its name.

The bearingless motor has become sufficiently well known to the person skilled in the art in the meantime and is used for a number of different applications. Some fundamental descriptions can be found, for example, in EP-A-0 860 046 and EP-A-0 819 330.

Centrifugal pumps, which are designed according to the principle of the bearingless motor, have proven themselves in a large number of applications.

SUMMARY

It has been found that due to the absence of mechanical bearings, a centrifugal pump, which is designed according to the principle of the bearingless motor, is particularly suitable for such applications in which the very sensitive substances mentioned at the beginning are conveyed, for example as blood pumps, or as pumps in which very high demands are made with respect to purity, for example in the pharmaceutical industry or in the biotechnological industry, or also for applications where abrasive or aggressive substances are conveyed which would destroy mechanical bearings very quickly, for example pumps for slurry or acidic fluids in the semiconductor industry.

Examples of such applications are extracorporeal membrane oxygenation (ECMO), in which blood is continuously transported through a membrane oxygenator, which replaces the gas exchange in the lungs, removes carbon dioxide from the blood and enriches the blood with oxygen. Furthermore, there are also machines that take over the function of the lungs during operations as heart-lung machines (CPB, cardiopulmonary bypass). In biotechnology, for example, pumps are needed to circulate nutrient liquids through a bioreactor or to move fluids through filter units, wherein the substrate to be generated is extracted in the filter units.

In these applications, in particular in medical technology and biotechnological applications, a redundancy must of course be provided, because if the pumping device fails, it must of course be ensured that the patient or the substance to be created is not endangered. It is therefore common practice to keep a second, usually identical pumping device ready to replace the defective pumping device and take over its function if it fails.

In all these applications, centrifugal pumps designed according to the principle of the bearingless motor have proven to be successful, in particular because no mechanical bearings are provided here, which can have a negative influence on the purity of the process.

A further advantage of the principle of the bearingless motor is the design of the rotor as an integral rotor, which is both the rotor of the electromagnetic drive and the rotor of the centrifugal pump. In addition to the magnetic levitation without contact, the advantage here is a very compact and space-saving design.

In addition, the principle of the bearingless motor also allows designs of centrifugal pumps in which the rotor or the pump housing with the rotor arranged in it can be separated from the stator very easily. This is a very great advantage, because in this way, for example, the pump housing with the rotor arranged in it can be designed as a single-use part for single use. Today, such single-use applications often replace processes in which, due to the very high purity requirements, all those components that come into contact with the fluids to be treated in the process previously had to be cleaned and sterilized in an elaborate manner, for example by means of steam sterilization. When designed for single use, those components that come into contact with the fluids to be treated are only used exactly once and are then replaced with new, i.e. unused, single-use parts for the next application.

A problem that arises when using centrifugal pumps for conveying such sensitive substances as blood or other biological fluids is the interaction between the vanes of the rotor and the fluids to be conveyed. In this respect, there are two aspects in particular which cause damage to the cells present in the fluid, for example the red blood cells, namely the shear force acting on the cells or other particles and the dwell time of the shear force, i.e. the time during which the particles are exposed to this shear force. In the meantime, it is known that the magnitude of the shear force is the more important factor with regard to the damage in the conveyed fluid.

Starting from this state of the art, it is therefore an object of the present disclosure to propose a pumping device which, on the one hand, enables the conveying of very sensitive fluids, such as fluids containing cells, with the least possible damage to the fluids and, on the other hand, has a redundancy. Furthermore, a single-use part for such a pumping device shall be proposed and a method for operating such a pumping device.

The subjects of the disclosure meeting these objects are characterized by the features described herein.

According to an embodiment of the invention, a pumping device for conveying a fluid is thus proposed, with a single-use device designed for single use and with a reusable device designed for multiple use, wherein the single-use device is designed to be inserted into the reusable device and comprises two pump units arranged in series one behind the other, wherein each pump unit comprises a rotor for conveying the fluid, wherein each rotor is designed as a rotor of a bearingless motor, and can be magnetically levitated without contact and driven without contact for rotation about an axial direction, wherein the reusable device is designed for inserting the single-use device and comprises for each rotor a stator which forms with the rotor an electromagnetic rotary drive for rotating the rotor about the axial direction, wherein each stator is designed as a bearing and drive stator with which the rotor can be magnetically driven without contact and can be magnetically levitated without contact with respect to the stator, and wherein an independent control device is provided for each stator which is designed for an independent activation of the respective stator.

The reusable device, which is designed for multiple use, is therefore designed in such a way that the single-use device can be inserted into the reusable device, enabling a very easy assembly and separation of the reusable device and the single-use device. Since the pumping device according to the embodiment of the invention comprises two pump units arranged in series, for a predetermined pressure to be generated by the pumping device, the two rotors can be operated at a lower rotational speed than if the same pressure has to be generated with only one pump unit, i.e. with only one rotor. It is known that damage to cells—for example red blood cells—contained in a biological fluid which is conveyed by a centrifugal pump increases disproportionately with the rotational speed of the centrifugal pump. The rotational speed at which the centrifugal pump is operated is the decisive factor for the magnitude of the shear force to which the biological cells in the fluid are subjected. The magnitude of this shear force in turn is the essential factor which is responsible for the damage or destruction of the cells.

It is known that in a centrifugal pump the generated pressure, more precisely the pressure difference between the pressure at the inlet of the pump and the pressure at the outlet of the pump, is at least in very good approximation proportional to the square of the rotational speed. However, this means that if a pressure difference is generated with two identical pump units connected in series, the rotational speed for each pump unit can be reduced by a factor of one by the root of two ($1/\sqrt{2}$), i.e. each of the two pump units is operated at a rotational speed which is about 0.71 times the rotational speed at which a single pump unit would have to be operated if it was to generate the same pressure difference. This reduction of the rotational speed considerably reduces the damage to cells in the fluid to be conveyed.

Since, in addition, an independent control device is provided for each stator so that each stator can be activated independently, the pumping device according to the invention enables a hot redundancy so that no replacement pumping device has to be kept available. In normal, i.e. trouble-free operation, the two pump units connected in series together generate the desired pressure difference. If one of the two pump units now fails, the rotational speed of the other pump unit is increased by a factor of root two ($\sqrt{2}$), i.e. by a factor of about 1.41, so that the desired pressure difference is now generated by this other pump unit alone. This hot redundancy, which allows an independent activation of each stator, is a significant advantage in particular in medical applications such as blood pumping and biotechnological applications such as cell cultivation.

According to a preferred embodiment, the single-use device has two cup-shaped protuberances in each of which a rotor is provided, and the reusable device has two recesses, each of which is designed to receive one of the cup-shaped protuberances. This embodiment enables a particularly easy assembly and separation of the single-use device and the reusable device.

It is a preferred embodiment that the reusable device is designed in such a way that, in the operating state, the rotors of the single-use device each rotate about an axis of rotation which encloses with the vertical an angle different from zero, which is smaller than 90°. In this embodiment, in the operating state, the two pump units are then arranged one behind the other in a plane that is inclined to the horizontal and inclined to the vertical. This embodiment is particularly advantageous for priming the pump unit, as it is more effective in preventing gas bubbles from sticking as in a siphon, for example in the flow connection between the two pump units.

According to a preferred embodiment, each pump unit is configured as a radial pump unit. The first pump unit has a first inlet and a first outlet for the fluid, the second pump unit has a second inlet and a second outlet for the fluid, wherein each inlet is designed such that the fluid flows to the respective rotor from an axial direction, and wherein each outlet is designed such that the fluid leaves the respective pump unit in a discharge direction which is aligned perpendicular to the axial direction.

In a first embodiment, the single-use device of the pumping device is designed in such a way that the fluid is diverted between the first outlet and the second inlet by at least 90° and preferably by 90°. If this single-use device is aligned in such a way that the axes of rotation of the pump units are aligned in the vertical direction (direction of gravity), the two pump units are arranged offset with respect to the axial direction. The fluid leaves the first pump unit in a discharge direction which extends perpendicular to the axial direction, is then diverted by 90° and then flows in a vertical direction through the second inlet of the second pump unit.

In a second embodiment, the single-use device of the pumping device is designed in such a way that the fluid is diverted between the first outlet and the second inlet by a total of 270°. If this single-use device is aligned in such a way that the axes of rotation of the pump units are aligned in the vertical direction (direction of gravity), the two pump units are arranged at the same height with respect to the vertical direction, i.e. next to each other. The fluid leaves the first pump unit in a discharge direction which extends perpendicular to the vertical direction, is then first diverted by 90° in the vertical direction upwards, then again by 90° in a direction perpendicular to the vertical direction (horizontal direction), then by 90° in the vertical direction downwards, and finally flows in a vertical direction through the second inlet of the second pump unit.

It is an advantageous measure that a separate power supply is provided for each stator in each case, so that if one of the power supplies fails, one of the stators can still be supplied with power. Thus, each stator as well as the control device assigned to it and, if necessary, other components, which are assigned to this stator, are also completely independent of the power supply, i.e. they can not only be activated but also supplied with power completely independent of the state of the other stator or the other stators.

As an advantageous option, a superordinate control unit can be provided, which is signal-connected to all control devices for the stators.

A further advantageous option is that an emergency energy store is provided from which energy can be supplied to each stator if a primary energy source for supplying the stators can no longer provide energy to one or all pump units.

The primary energy source can, for example, be designed as a power supply unit that receives electrical power from an external power supply system. The emergency energy store can be designed as an accumulator or a battery, for example, and also provides energy even if the power supply unit is not connected to an external power supply system or if the power supply unit is defective. This accumulator or this battery is very advantageous, for example, when a patient is connected to the pumping device and must be transported from one place to another.

Preferably, each power supply comprises both a primary energy source designed as a power supply unit that can be connected to an external power supply system and an accumulator or a battery as an emergency energy store.

It is a further advantageous measure that the single-use device and/or the reusable device contain an identification element with which the single-use device and the reusable device can exchange information with each other. In particular, each identification element can also be designed as RFID (radio-frequency identification) or as a barcode, in particular as a two-dimensional or three-dimensional barcode.

Furthermore, a single-use device is proposed by embodiments of the invention, which is designed for single use and for a pumping device, which is designed according to embodiments of the invention.

A method for operating a pumping device is also proposed by an embodiment of the invention, wherein a desired value for an operating parameter of the pumping device is predetermined to each control device, wherein an actual value for this operating parameter is determined by a sensor and wherein the actual value is transmitted to each control device.

Preferably, the control devices exchange signals with each other, by which each control device can determine the functioning of the other pump unit.

A preferred operating parameter is the flow through the pumping device, or the pressure difference generated by the pumping device.

It is an advantageous option that the flow through the pumping device is determined from the rotational speed and the torque at which the rotors are driven.

Further advantageous measures and embodiments of the invention are described herein.

BRIEF DESCRIPTION OF THE DRAWINGS

The invention will be explained in more detail hereinafter with reference to the drawings.

DETAILED DESCRIPTION

In the following description of the invention on the basis of embodiments, examples thereof and variants, the same parts or functionally equivalent parts are designated throughout by the same reference signs. It is understood that the explanations with respect to an example of an embodiment or a specific embodiment or a specific variant apply in the same manner or in the analogously same manner also to the other embodiments, examples thereof and variants. This means that only the differences to the embodiments, examples thereof or variants described above will be discussed in more detail.

Figure 1:
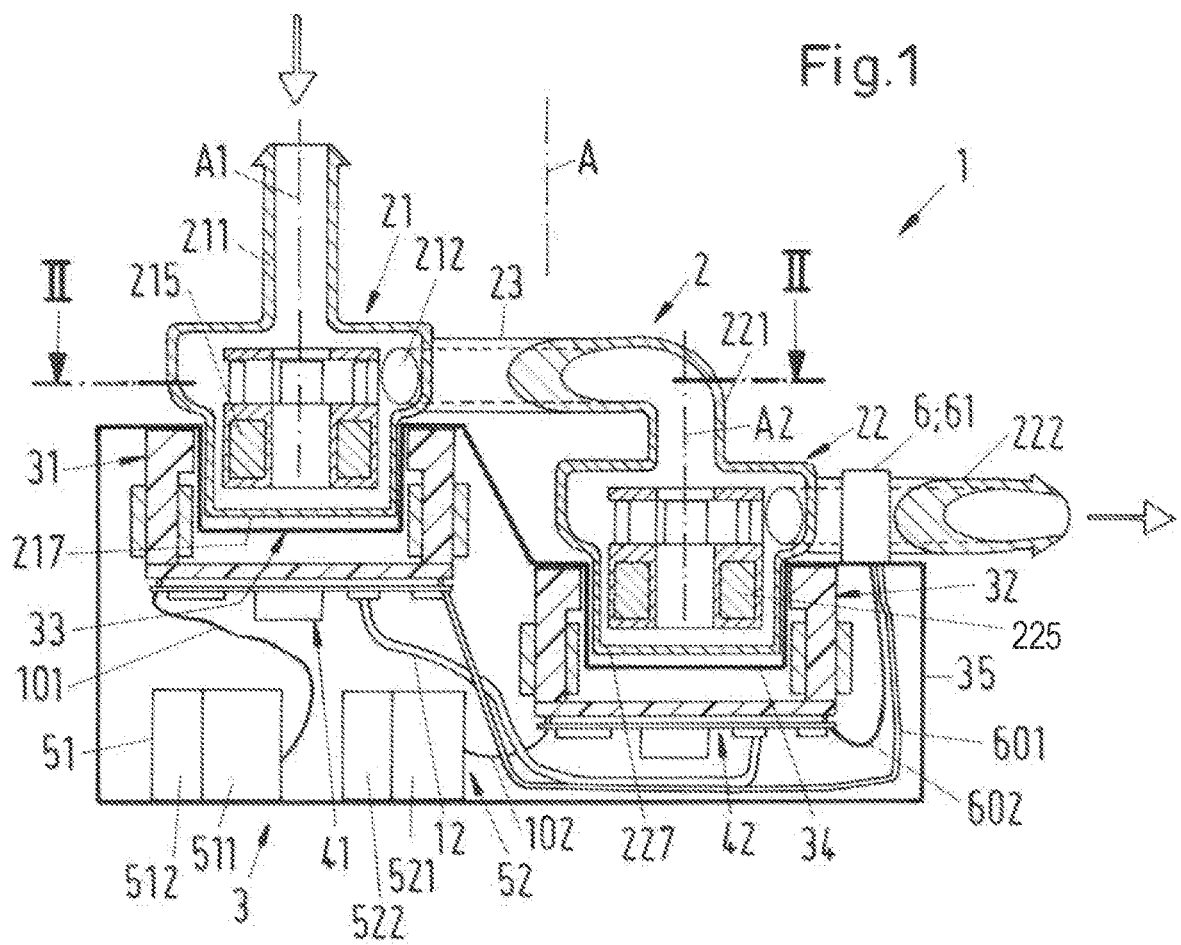
FIG. 1 is a schematic sectional representation of a first embodiment of a pumping device according to the invention in a section along the section line I-I in FIG. 2.
Figure 2:
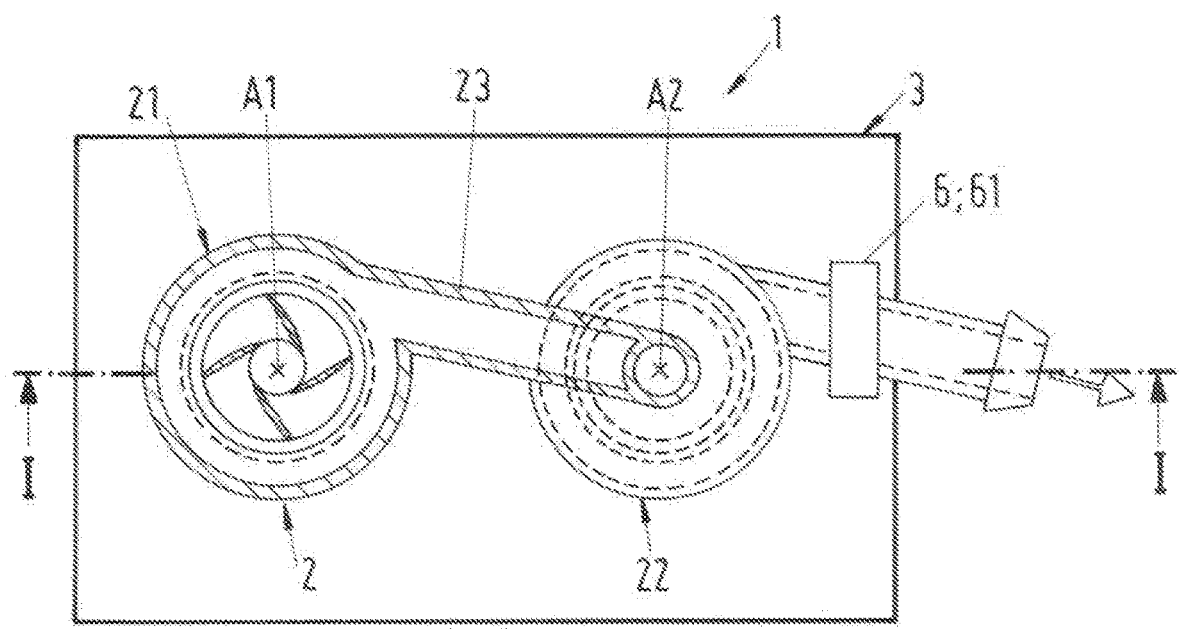
FIG. 2 is a schematic sectional representation of the first embodiment in a section along the section line II-II in FIG. 1.

FIG. 1 shows in a schematic sectional representation a first embodiment of a pumping device according to the invention, which is designated as a whole by the reference sign 1. For better understanding, FIG. 2 still shows a schematic sectional representation of the first embodiment of a pumping device 1 according to the invention, wherein the section is made along the section line II-II in FIG. 2. In FIG. 2, the section line I-I is drawn for the sectional representation shown in FIG. 1.

In order to ensure the purity or sterility of those components that come into contact with the fluid to be conveyed, for example blood or another biological fluid, the pumping device 1 has a single-use device, which is designated as a whole by the reference sign 2 and is designed for single use, and a reusable device, which is designated as a whole by the reference sign 3 and is designed for permanent use, i.e. multiple use. The single-use device 2 comprises those components which come into contact with the fluid to be conveyed during the operation of the pumping device 1.

The term "single-use device" and other compositions with the component "single-use", such as single-use part, single-use component etc., refer to those components or parts which are designed for single use, i.e. which can only be used once as intended and are then disposed of. For a new application, a new, previously unused single-use part must then be inserted. When configuring or designing the single-use device 2, there are therefore essential aspects that the single-use device 2 can be produced as simply and economically as possible, and that it causes low costs. Another essential aspect is that the single-use device 2 can be assembled with the reusable device 3 and separated from the reusable device 3 as easily as possible. The single-use device 2 should therefore be able to be replaced very easily without the need for high assembly efforts. Particularly preferred, the single-use device 2 should be able to be assembled with and separated from the reusable device 3 without the use of tools.

For this reason, the single-use device 2 is designed to be inserted into the reusable device 3, and the reusable device 3 is designed to receive the single-use device 2, i.e. in such a way that the single-use device 2 can be inserted into the reusable device 3.

Figure 3:
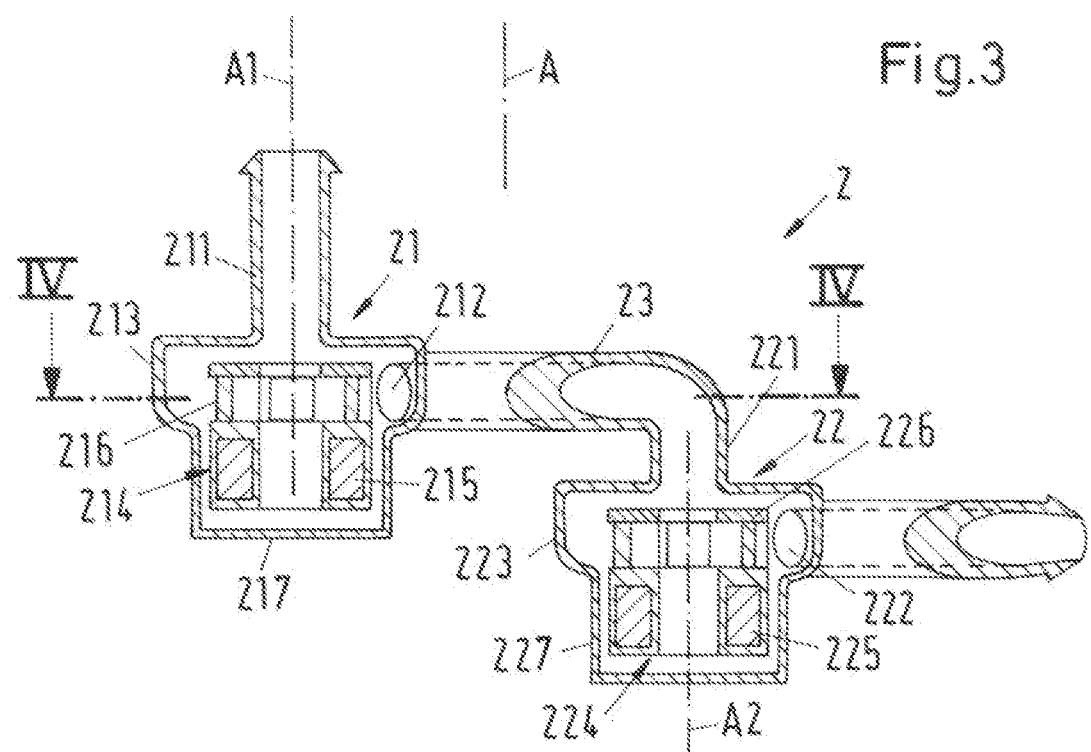
FIG. 3 is a schematic sectional representation of the first variant for the single-use device in a section along the section line III-III in FIG. 4.
Figure 4:
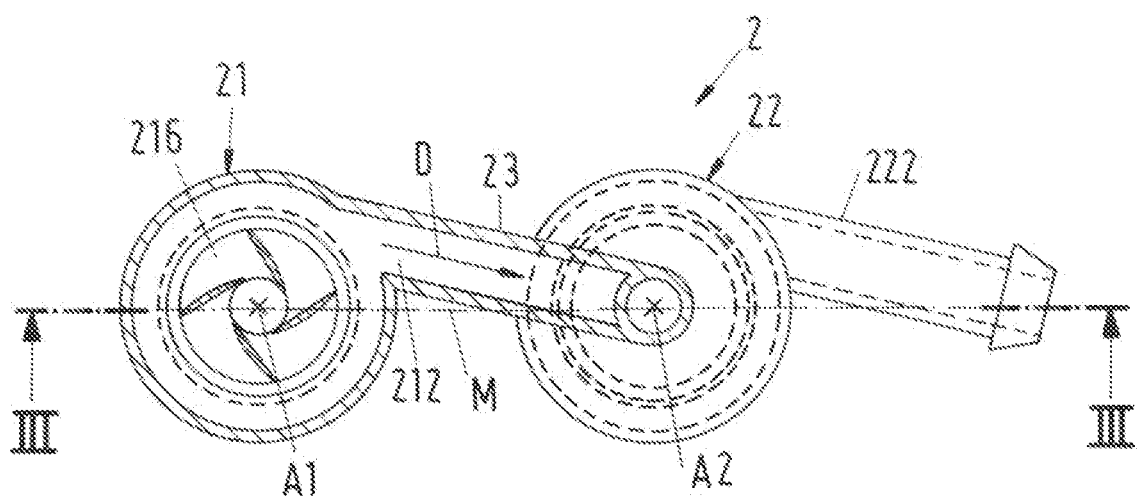
FIG. 4 is a schematic sectional representation of the first variant for the single-use device in a section along the section line IV-IV in FIG. 3.

The single-use device 2 is designed according to a first variant, which is represented in FIG. 3 and FIG. 4 in two schematic sectional representations. FIG. 3 shows the first variant of the single-use device 2 in a section along the section line III-III in FIG. 4, and FIG. 4 shows the first variant of the single-use device in a section along the section line IV-IV in FIG. 3.

The single-use device 2 comprises two pump units, namely a first pump unit 21 and a second pump unit 22. The first pump unit 21 comprises a first inlet 211 and a first outlet 212 for the fluid to be conveyed. The second pump unit 22 comprises a second inlet 221 and a second outlet 222 for the fluid to be conveyed. The two pump units 21, 22 are arranged in series or one behind the other, i.e. the first outlet 212 is flow-connected to the second inlet 221 by means of a connecting channel 23. In the operating state, the fluid therefore flows through the first inlet 211 into the first pump unit 21, flows through it and leaves the first pump unit 21 through the first outlet 212. From there, the fluid is passed through the connection channel 23 to the second inlet 221, flows through the second pump unit 22 and leaves it through the second outlet 222, as represented by the two arrows without reference signs in FIG. 1.

Each pump unit 21, 22 comprises a pump housing 213 or 223 (FIG. 3) in each case, in which a rotor 214 or 224 is provided in each case for conveying the fluid, which forms the respective impeller of the pump unit 21. Each rotor 214, 224 is simultaneously designed as a rotor 214, 224 of an electromagnetic rotary drive, each configured according to the principle of a bearingless motor, which will be explained further on. For this purpose, each rotor 214, 224 comprises a magnetically effective core 215 or 225 in each case, which for example can be made as a permanent magnetic ring or also as a ring of a soft magnetic material, for example iron. Usually, this magnetically effective core 215 or 225 is completely sheathed or encapsulated, whereby the sheathing is preferably made of a plastic. An impeller 216 or 226 is then provided on this sheathing in each case, which acts on the fluid to be conveyed with a plurality of vanes.

Preferably, each pump unit 21, 22 is designed as a radial centrifugal pump, in which the respective rotor 214, 215 rotates about an axis of rotation A1 or A2. The fluid flows to the respective rotor 214, 215 in the direction of the respective axis of rotation A1 or A2 and deflects the fluid in a discharge direction D (FIG. 4), which is perpendicular to the respective axis of rotation A1 or A2.

Preferably—but not necessarily—the two pump units 21, 22 are designed identically at least with respect to their hydraulics. Particularly preferred, the axes of rotation A1 and A2 are parallel to each other. This common direction, in which the two parallel axes of rotation A1, A2 extend, is designated in the following as axial direction A. A direction perpendicular to it is designated as radial direction.

Furthermore, it is preferred that the two pump units 21, 22 are rigidly connected to each other by the connecting channel 23, so that the two pump units 21, 22 form a structural unit with the connecting channel 23, which can be inserted as a whole into the reusable device 3.

The longitudinal direction of the connecting channel 23 determines the discharge direction D (FIG. 4), in which the fluid leaves the first pump unit 21. The connecting channel 23 is aligned such that the discharge direction D is on the one hand perpendicular to the axial direction A and on the other hand forms an angle different from 0° and 90° with an imaginary shortest connecting line M between the two axes of rotation A1 and A2. In the representation in FIG. 4, the connecting line M lies on the section line III-III.

As can be seen in particular in FIG. 1 and FIG. 3, in the first variant of the single-use device 2, the connecting channel 23 is designed in such a way that the fluid is diverted by 90° with respect to the axial direction A between the first outlet 212 and the second inlet 221. The connecting channel 23 extends downstream of the first outlet 212, first perpendicular to the axial direction A, so that the discharge direction D is perpendicular to the axial direction A. Subsequently, the connecting channel 23 bends downwards by 90°, whereby "below" or "downwards" refers to the representation in FIG. 1 and in FIG. 3, so that the fluid flows through the second inlet 221 in the axial direction A. This embodiment has the consequence that in the position of use represented in FIG. 1, in which the axes of rotation A1, A2 of the pump units 21, 22 are each aligned in the vertical direction (direction of gravity), the two pump units 21, 22 are arranged offset with respect to the vertical direction.

Each pump unit 21, 22 has a pot-shaped or cup-shaped protuberance 217 or 227, which is here formed by the respective pump housing 213 or 223 in each case. Each rotor 214, 224 is arranged in the associated pump housing 213 or 223 in such a way that at least the magnetically effective core 215 or 225 of the respective rotor 214, 224 is arranged in the respective cup-shaped protuberance 217 or 227.

The reusable device 3 (FIG. 1) comprises a stator housing 35 in which two stators, namely a first stator 31 and a second stator 32, are provided for interacting with one of the rotors 214 or 224. The reusable device 3 further comprises two pot-shaped or cup-shaped recesses 33 or 34, which are disposed in the stator housing 35 and which are dimensioned and arranged such that each of the cup-shaped recesses 33, 34 can receive and enclose one of the cup-shaped protuberances 217, 227 of the single-use device 2 in each case. The dimensions of each recess 33, 34 and each protuberance 217, 227 are matched to each other in such a way that each recess 33, 34 closely encloses one of the protuberances 217, 227 in the assembled state and its shell surface abuts against the shell surface of the respective protuberance 217, 227.

The two stators 31, 32 are each arranged around one of the recesses 33 or 34 and enclose the respective recess 33, 34 as closely as possible. Each stator 31, 32 is arranged such that in the assembled state of the pumping device 1 each of the magnetically effective cores 215, 225 is surrounded by a respective one of the stators 31, 32 or is surrounded by the stator poles of the stator 31 or 32 so that the best possible magnetic interaction between the respective stator 31, 32 and the respective magnetically effective core 215, 225 is given.

The embodiment with the protuberances 217, 227 in the single-use device 2 and the recesses 33, 34 in the reusable device 3 enables a particularly easy connection or separation of the single-use device 2 and the reusable device 3. The two protuberances 217 and 227 with the rotors 214, 224 arranged therein are inserted in a simple way into the two recesses 33, 34 and the pumping device 1 is ready for operation. In the same simple way, the two protuberances 217, 227 can be pulled out of the recesses 33, 34, thus separating the single-use device 2 from the reusable device 3. Of course, safety elements such as a snap connection can be provided to prevent an unintentional separation of the single-use device 2 and the reusable device 3.

As already mentioned, the two rotors 214, 224 and the two stators 31, 32 are designed in such a way that the first stator 31 and the first rotor 214 as well as the second stator 32 and the second rotor 224 form an electromagnetic rotary drive which is designed as a bearingless motor.

For this purpose, each stator 31, 32 is designed as a bearing and drive stator with which the respective rotor 214, 224 can be magnetically driven without contact for rotation about the respective axis of rotation A1, A2 and can be magnetically levitated without contact with respect to the stator 31, 32.

Since the two axes of rotation A1, A2 are parallel, reference is made in the following to the axial direction A.

The magnetically effective core 215 or 225 of the rotor 214 or 224, which can be designed in the form of a circular disk, or a circular cylinder, or be annular, refers to that area of the rotor 214, 224 which interacts with the respective stator 31, 32 for torque formation and for generating the magnetic bearing forces. Depending on the design, the magnetically effective core 215, 225 can comprise one or more permanent magnets. As an alternative, it is also possible to design the magnetically effective core 215, 225 without permanent magnets, for example as a reluctance rotor. In this embodiment, the magnetically effective core 215, 225 includes at least partially of a ferromagnetic material, for example iron.

The respective rotary drive with the first rotor 214 and the first stator 31 or with the second rotor 224 and the second stator 32 is designed as a so-called temple motor, for example.

The characteristic feature of an embodiment as a temple motor is that the stator 31, 32 comprises a plurality of separate coil cores each comprising a bar-shaped longitudinal leg, which extends from a first end in the axial direction A to a second end, wherein all first ends are connected by a yoke. Furthermore, each coil core comprises a transverse leg which is arranged at the second end of the respective longitudinal leg and which extends in the radial direction, i.e. perpendicular to the axial direction A and thus perpendicular to the respective longitudinal leg. Each transverse leg extends inward in the radial direction, i.e. towards the respective rotor 214, 224. Thus, each coil core has an L-shaped design, wherein the longitudinal legs each form the long leg of the L extending in the axial direction A, and the transverse legs extending perpendicular to the longitudinal legs in the radial direction towards the rotor 214, 224 each form the short leg of the L.

The radially inner ends of the transverse legs each form a stator pole. The stator poles are arranged ring-shaped around the respective recess 33, 34 with the rotor 214 or 224 inside. In the operating state, the stator poles and the magnetically effective core 215 or 225 are at the same level with respect to the axial direction A, if the rotor 214, 224 is not deflected from its nominal position.

The parallel longitudinal legs of the coil cores, which all extend parallel to the axial direction A, and which surround the rotor 214 or 224, are what gave the temple motor its name, because these parallel longitudinal legs are reminiscent of the columns of a temple.

Each stator 31, 32 further comprises a plurality of windings for generating electromagnetic rotating fields, with which the respective rotor 214, 224 can be magnetically driven without contact and magnetically levitated without contact with respect to the stator 31 or 32. The windings are, for example, designed as individual coils, wherein one coil is disposed on each of the longitudinal legs of a stator 31, 32. Each coil is arranged around the respective longitudinal leg so that the coil axis is parallel to the axial direction A in each case.

Each temple motor is designed according to the principle of a bearingless motor. This means that during operation of the pumping device 1 the respective magnetically effective core 215, 225 of the rotor 214, 224 interacts with the respective stator 31, 32 according to the principle of the bearingless motor described above, in which the respective rotor 214, 224 can be magnetically driven without contact and magnetically levitated without contact with respect to the respective stator 31, 32.

The principle of the bearingless motor is sufficiently well known to the person skilled in the art in the meantime, so that a more detailed description of the function is no longer necessary. The principle of the bearingless motor means that the rotor 214, 224 can be magnetically driven and magnetically levitated, wherein the stator 31, 32 is designed as a bearing and drive stator, which is both the stator of the electric drive and the stator of the magnetic levitation. For this purpose, the stator 31 or 32 comprises the windings in each case with which both the drive function and the bearing function are realized. An electromagnetic rotating field can be generated by the windings, which on the one hand exerts a torque on the magnetically effective core 215, 225 of the rotor 214, 224, which causes its rotation about the axial direction A, and which on the other hand exerts an arbitrarily settable shear force on the magnetically effective core 215, 225 of the rotor 214, 224, so that its radial position—i.e. its position in the radial plane perpendicular to the axial direction A—can be actively controlled or regulated. In the case of a bearingless motor, in contrast to classical magnetic bearings, the magnetic levitation and the drive of the motor is realized via electromagnetic rotating fields, which exert a torque and a settable shear force on the magnetically effective core of the rotor. The rotating fields required for this can either be generated with different coils, or the rotating fields can be generated by mathematical superposition of the required fluxes and then with the aid of a single coil system. In the case of a bearingless motor, it is therefore not possible to divide the electromagnetic flux generated by the windings of the stator 31, 32 into an electromagnetic flux, which only provides the drive of the rotor 214, 224 and an electromagnetic flux which only realizes the magnetic levitation of the rotor 214, 224.

According to the principle of the bearingless motor, at least three degrees of freedom of the rotor 214, 224 can be actively regulated, namely its position in the radial plane and its rotation about the axial direction A. With respect to its axial deflection in the axial direction A, the magnetically effective core 215, 225 of the rotor 214, 224 is passively magnetically stabilized by reluctance forces, i.e. it cannot be activated. With respect to the remaining two degrees of freedom, namely tilting with respect to the radial plane perpendicular to the axis of rotation A1, A2, the rotor 214, 224 is also passively magnetically stabilized. By the interaction of the magnetically effective core 215, 225 with the stator 31, 32, the rotor 214, 224 is thus passively magnetically levitated or passively magnetically stabilized in the axial direction A and against tilting (three degrees of freedom in total) and actively magnetically levitated in the radial plane (two degrees of freedom). In this way, the respective rotor 214, 224 can be magnetically driven without contact for rotation about the respective axis of rotation A1, A2, and can be magnetically levitated without contact with respect to the respective stator 31, 32.

It is a substantial aspect of the pumping device 1 according to an embodiment of the invention that an independent control device 41, 42 is provided for each stator 31, 32, namely a first control device (electronic controller) 41 for the first stator 31 and a second control device (electronic controller) 42 for the second stator 32. Each control device 41, 42 is designed in such a way that an independent activation of the respective stator 31, 32 is possible.

In principle, therefore, the first control device 41 does not require any information from the second control device 42 in order to operate the first stator 31 and the first rotor 214 according to the principle of the bearingless motor. Conversely, the second control device 42 does not require any information from the first control device 41 in order to operate the second stator 32 and the second rotor 224 according to the principle of the bearingless motor.

This means that if one of the control devices 41 or 42 fails, the pumping device 1 is still working because the operation of the pumping device 1 can be maintained by the other control device 42 or 41. Thus, the pumping device 1 according to embodiments of the invention can be designed to be hot redundant.

Preferably, each control device 41 or 42 is designed as an electronic board which is arranged below the respective stator 31, 32 and fixed to the respective stator 31, 32 according to the representation in FIG. 1. Each electronic board comprises all components required for the operation of the respective bearingless motor, such as the power electronics for activating the windings, as well as the necessary evaluation, regulation and activation components.

Furthermore, for each control device 41, 42 a power supply 51, 52 is provided which supplies the respective control device 41, 42 with power, preferably with electrical power, namely a first power supply 51 which supplies the first control device 41 with power and a second power supply 52 which supplies the second control device 42 with power. The first power supply 51 is connected to the first control device 41 via a first supply line 101 and the second power supply 52 is connected to the second control device 42 via a second supply line 102.

Preferably, the power supplies 51, 52 are arranged in the stator housing 35.

Each power supply 51, 52 comprises a primary energy source 511, 521 and an emergency energy store 512, 522. The primary energy source 511, 521 can, for example, be designed in each case as a power supply unit that receives electrical power from an external power supply system. The emergency energy store 512, 522 can be designed in each case as an accumulator or a battery, for example, and also provides energy even if the power supply unit is not connected to an external power supply system or if the power supply unit is defective. This accumulator or this battery are very advantageous, for example, when a patient is connected to the pumping device 1 and must be transported from one place to another.

In other embodiments, it is possible for only one common power supply to be provided, which supplies both control devices 41, 42 with electrical energy. Even in such embodiments, the common energy supply comprises both a primary energy source designed as a power supply unit that can be connected to an external power supply system and an accumulator or battery as an emergency energy store.

The pumping device 1 further comprises at least one sensor 6, with which an operating parameter of the pumping device 1 can be determined. The sensor 6, for example, is a flow sensor 61, with which the flow of the fluid through the pumping device 1 can be determined. The flow sensor 61, which for example is designed as an ultrasonic flow measuring device, can be arranged at or near the second outlet 222. It is possible that the flow sensor 61, or more generally the sensor 6, is part of the reusable device 3. Furthermore, it is possible that the flow sensor 61, or more generally the sensor 6, is part of the single-use device 2.

The sensor 6 is signal-connected to the first control device 41 by a first signal connection 601 and to the second control device 42 by a second signal connection 602. This also ensures the independence of the control devices 41, 42 from each other, as each control device 41, 42 receives the signal from the sensor 6 independently of the other control device 42, 41.

Preferably, a communication connection 12 is provided, via which the two control devices 41 and 42 can exchange signals or information with each other. This communication connection 12 can be used, for example, such that each control device 41, 42 can check the functioning of the other control device 42, 41 or the other pump unit 22, 21.

The single-use device 2—with the exception of the magnetically effective cores 215, 225—is preferably made of one or more plastics. In particular, the pump housings 213, 223, the inlets 211, 221, the outlets 212, 222, the connecting channel 23, the impellers 216, 226, the protuberances 217, 227 and the sheathings of the magnetic effective cores 215, 225 are made of plastic. Of course, not all components of the single-use device 2 have to be made of the same plastic.

The selection of suitable plastics naturally depends on the respective application. Suitable plastics are, for example: polyethylenes (PE), polypropylenes (PP), low density polyethylenes (LDPE), ultra-low density polyethylenes (ULDPE), ethylene vinyl acetates (EVA), polyethylene terephthalates (PET), poly vinylchloride (PVC), polyvinylidene fluorides (PVDF), acrylonitrile buta diene styrenes (ABS), polyurethane (PU), polyacrylic, polycarbonates (PC), silicones.

In the following, a second embodiment of the pumping device 1 according to the invention is explained on the basis of FIG. 5-FIG. 8, which shows a second variant for the single-use device 2. As already mentioned, only the differences to the first embodiment and the first variant are discussed in more detail.

Figure 5:
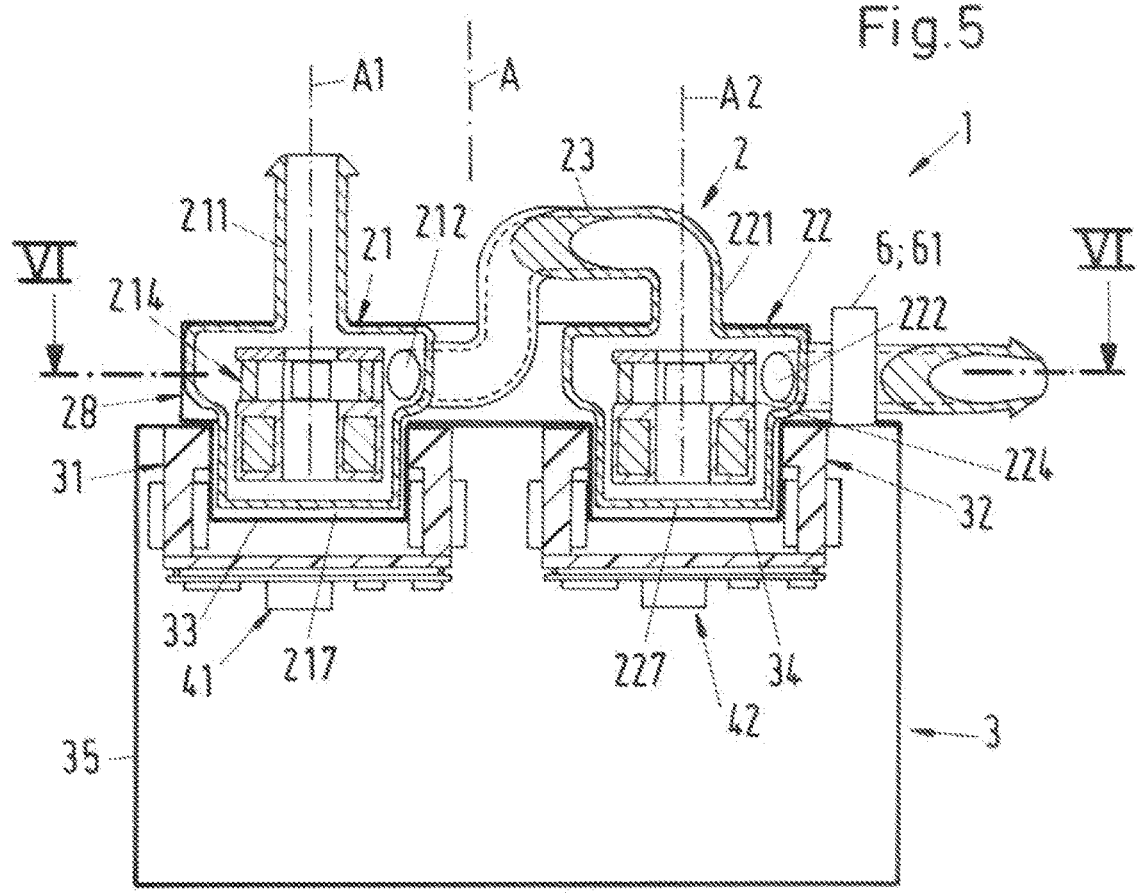
FIG. 5 is a schematic sectional representation of a second embodiment of a pumping device according to the invention in a section along the section line V-V in FIG. 6.
Figure 6:
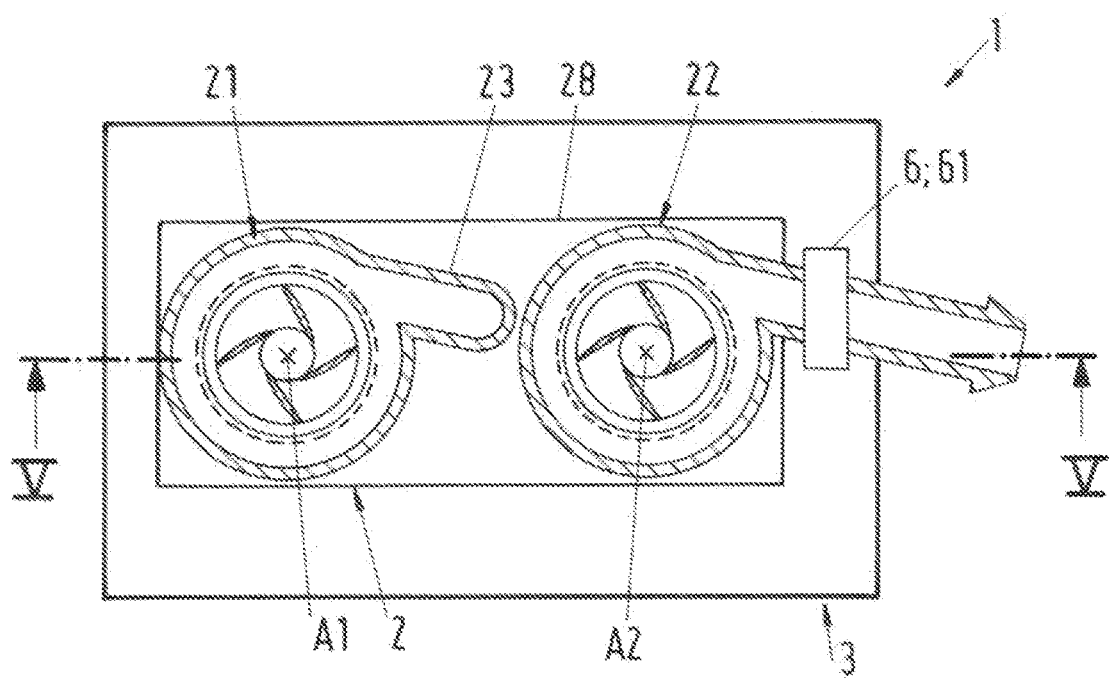
FIG. 6 is a schematic sectional representation of the second embodiment in a section along the section line VI-VI in FIG. 5.

FIG. 5 shows in a representation analogous to FIG. 1, a schematic sectional representation of the second embodiment of the pumping device 1 according to the invention in a section along the section line V-V in FIG. 6. However, in FIG. 5 the representation of the power supplies 51, 52 as well as the various connections in the stator housing 35 has been omitted because they are designed in an analogous manner to the first embodiment.

Figure 7:
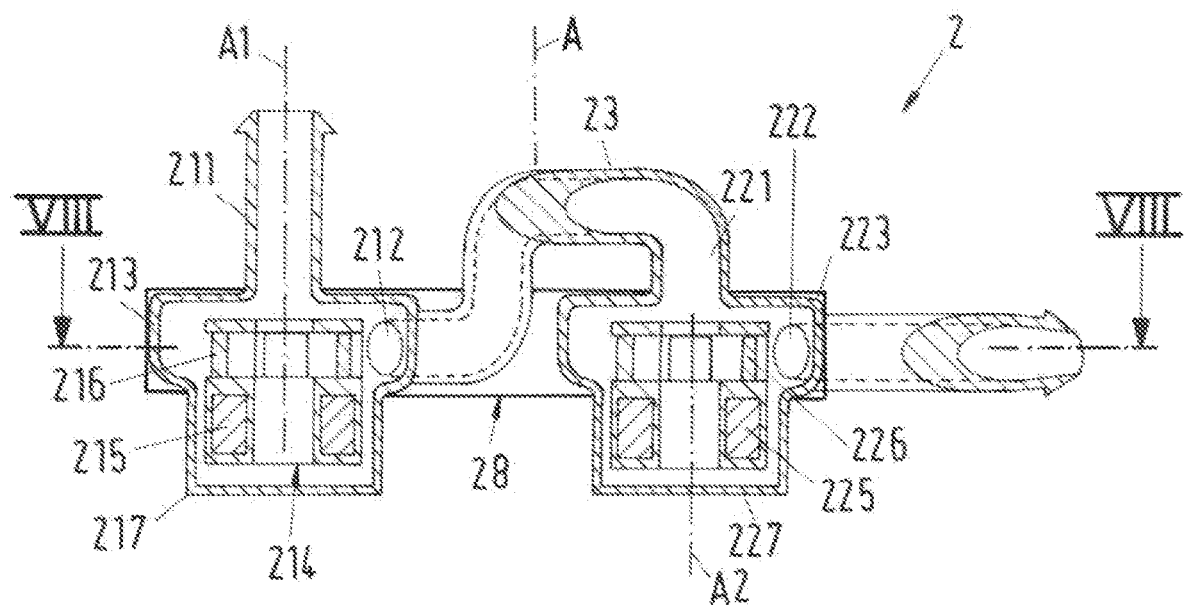
FIG. 7 is a schematic sectional representation of the second variant for the single-use device in a section along the section line VII-VII in FIG. 8.
Figure 8:
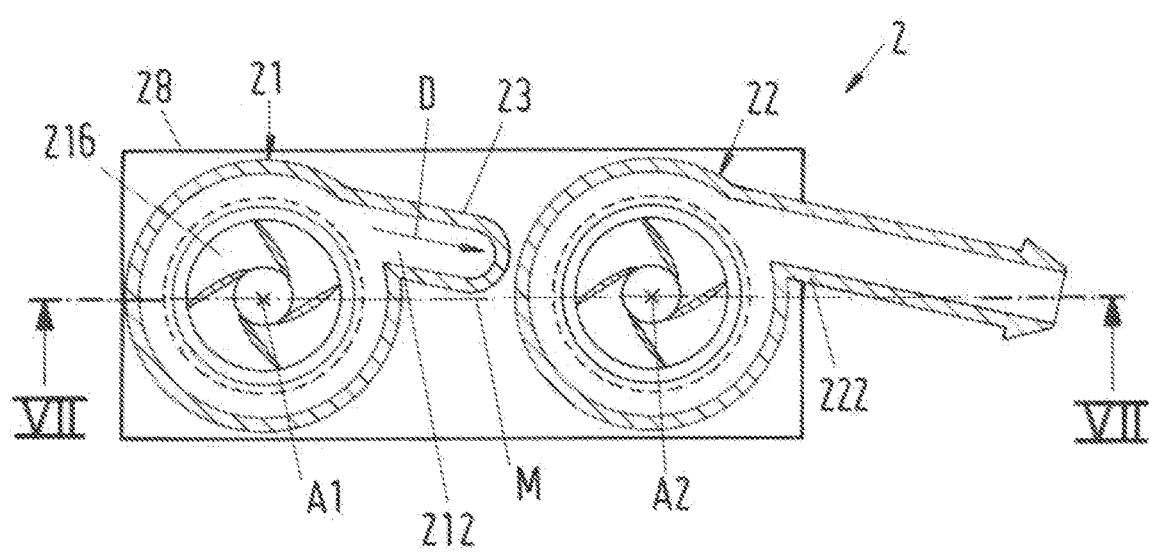
FIG. 8 is a schematic sectional representation of the second variant for the single-use device in a section along the section line VIII-VIII in FIG. 7.

FIG. 6 shows in a representation analogous to FIG. 2, a schematic sectional representation of the second embodiment of the pumping device 1 according to the invention in a section along the section line VI-VI in FIG. 5. FIG. 7 shows in a representation analogous to FIG. 3, a schematic sectional representation of the second variant for the single-use device 2 in a section along the section line VII-VII in FIG. 8. FIG. 8 shows in a representation analogous to FIG. 4, a schematic sectional representation of the second variant for the single-use device 2 in a section along the section line VIII-VIII in FIG. 7.

In the second variant of the single-use device 2, a single-use housing 28 is provided in which the pump units 21, 22 are arranged. The single-use housing 28, for example, forms a cassette which, as a single-use part, can be inserted into the reusable device 3 or separated from the reusable device 3 in a particularly simple way.

As can be seen in particular in FIG. 5 and FIG. 7, in the second variant of the single-use device 2, the connecting channel 23 is designed in such a way that the fluid is diverted by a total of 270° with respect to the axial direction A between the first outlet 212 and the second inlet 221. The connecting channel 23 is designed substantially in a U-shape. The connecting channel 23 extends downstream of the first outlet 212 first perpendicular to the axial direction A, so that the discharge direction D (FIG. 8) is perpendicular to the axial direction A. Subsequently, the connecting channel 23 bends upwards by 90°, wherein "above" or "upwards" refers to the representation in FIG. 5 and in FIG. 7. Then, the connecting channel 23 bends by 90° to the right, wherein "right" refers to the representation in FIG. 5 and in FIG. 7, whereby the connecting channel 23 is again perpendicular to the axial direction A. Finally, the connecting channel 23 bends downwards by 90°, wherein "below" or "downwards" refers to the representation in FIG. 5 and in FIG. 7, so that the fluid flows through the second inlet 221 in the axial direction A. This embodiment has the consequence that in the position of use shown in FIG. 5, in which the axes of rotation A1, A2 of the pump units 21, 22 are each aligned in the vertical direction (direction of gravity), the two pump units 21, 22 are arranged at the same height with respect to the vertical direction, i.e. next to each other. The reusable device 3 is adapted to this embodiment of the single-use device 2.

Figure 9:
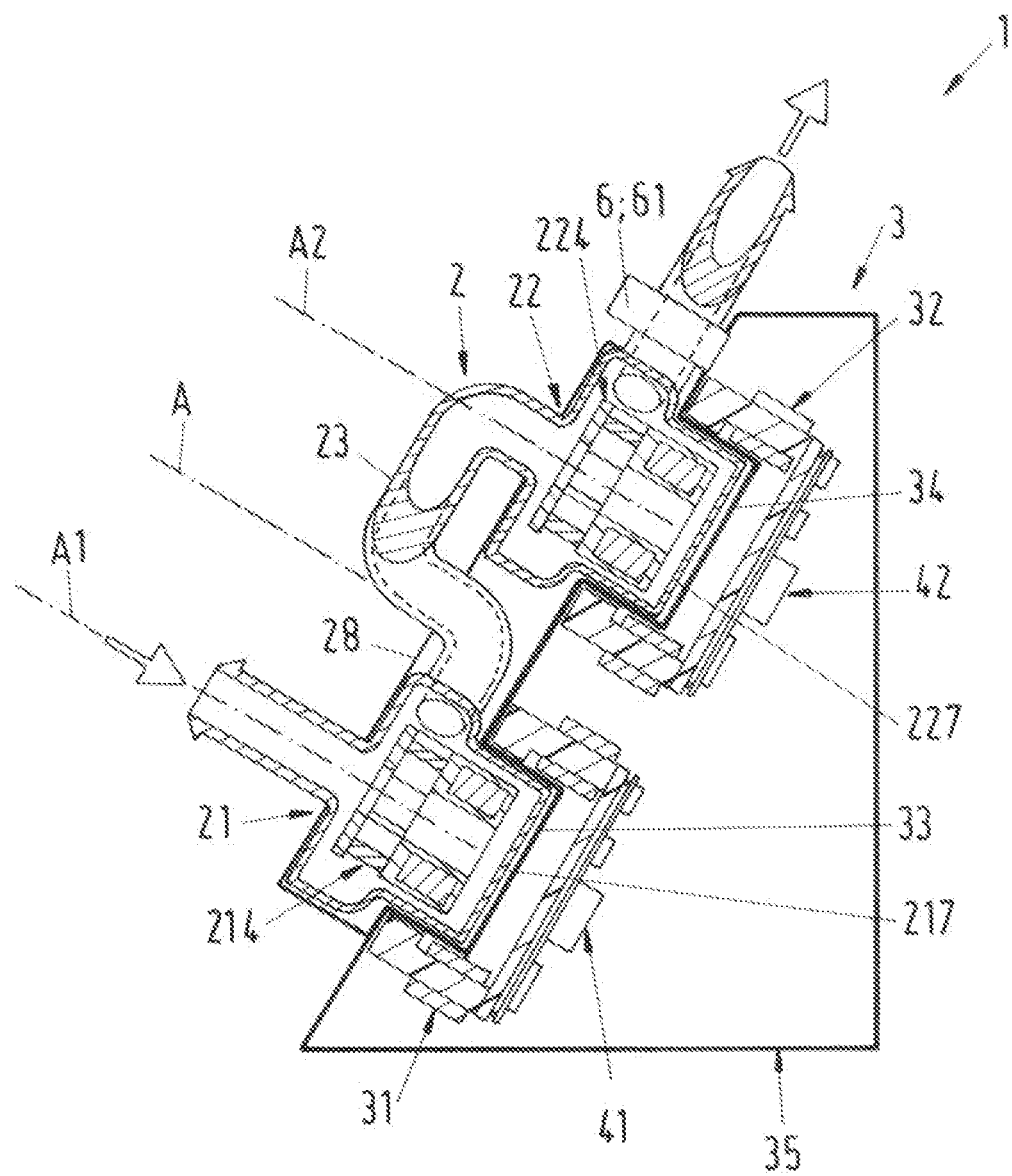
FIG. 9 is a schematic sectional representation of a third embodiment of a pumping device according to the invention in a section analogous to FIG. 5.

FIG. 9 shows a schematic sectional representation of a third embodiment of a pumping device 1 according to the invention in a section analogous to FIG. 5. The third embodiment of the pumping device 1 according to the invention comprises a single-use device 2 which is designed according to the second variant of the single-use device 2. It is understood that the third embodiment of the pumping device 1 according to the invention can also be provided in an analogously the same manner with a single-use device 2, which is designed according to the first variant for the single-use device 2.

The substantial difference to the previously described embodiments is that in the third embodiment of the pumping device 1 according to the invention, the reusable device 3 is designed in such a way that the rotors 214, 224 of the single-use device 2 each rotate about the axes of rotation A1, A2 in the operating state, wherein the axes of rotation A1 and A2 enclose with the vertical an angle different from zero, which is smaller than 90°. This means that the two axes of rotation A1 and A2 are inclined to the vertical at an angle different from zero and 90° in the operating state. The vertical corresponds to the vertical direction, i.e. the direction in which gravity acts.

With this embodiment, it is particularly easy to prevent gas bubbles, e.g. air bubbles, that stick in particular in the connection channel 23 during priming of the pumping device 1, Which could cause considerable damage during operation, for example to a patient connected to the pumping device 1. Sticking of gas bubbles, as is desirable in a siphon, for example, is efficiently prevented by the inclined position of the two pump units 21, 22 relative to the vertical and horizontal direction.

In FIG. 10 to FIG. 14, a fourth embodiment of a pumping device 1 according to the invention is explained, which has a third variant for the single-use device 2. Here too, only the differences to the previously described embodiments and variants are discussed in more detail.

It is understood that the fourth embodiment of the pumping device 1 according to the invention can also include a single-use device 2 in an analogously same manner, which is designed according to the first or second variant for the single-use device 2.

Figure 10:
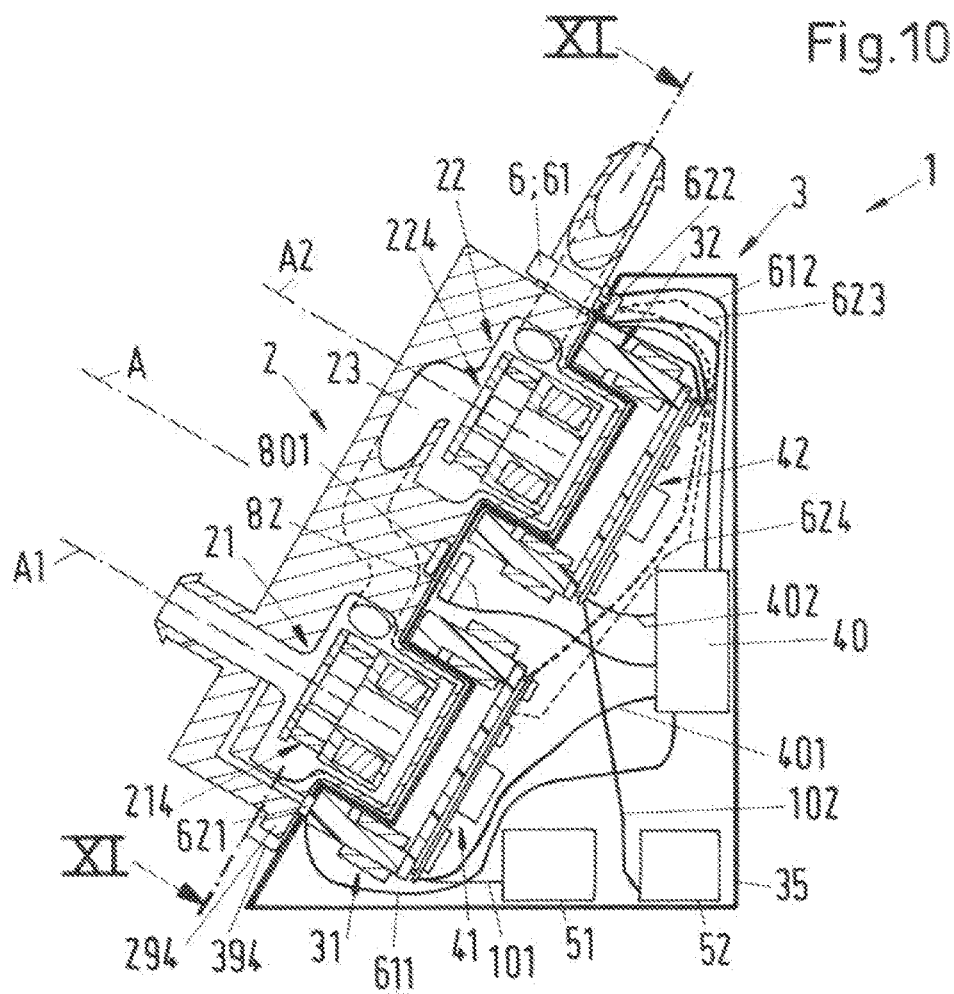
FIG. 10 is a schematic sectional representation of a fourth embodiment of a pumping device according to the invention in a section along the section line X-X in FIG. 11.
Figure 11:
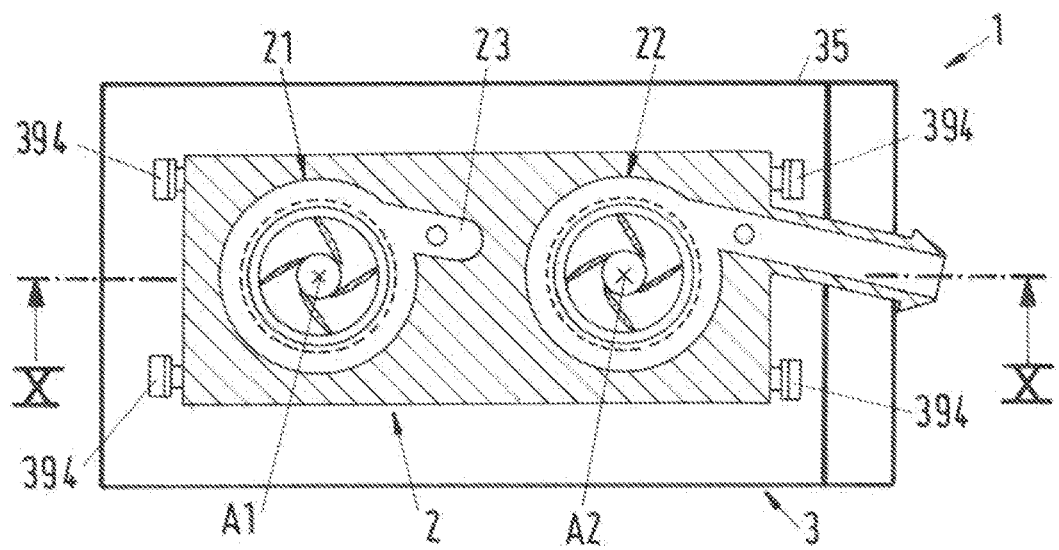
FIG. 11 is a schematic sectional representation of the fourth embodiment of a pumping device according to the invention in a section along the section line XI-XI in FIG. 10.
Figure 12:
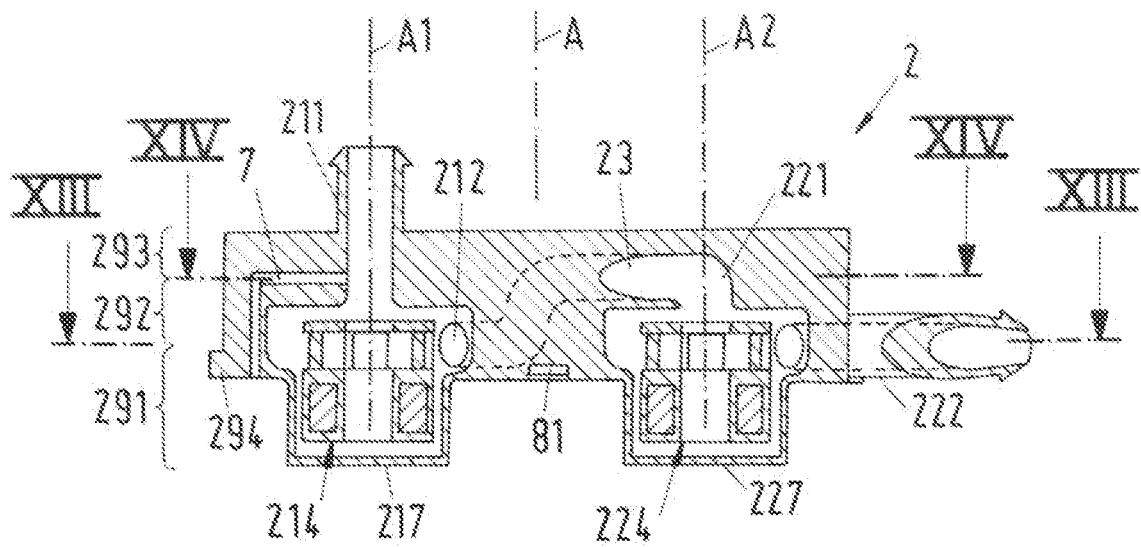
FIG. 12 is a schematic sectional representation of the third variant for the single-use device in a section along the section line XII-XII in FIG. 13.
Figure 13:
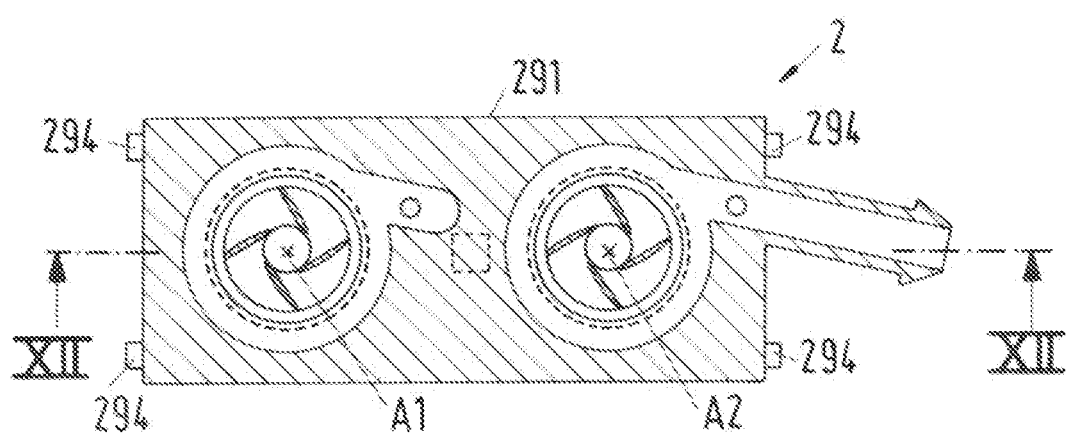
FIG. 13 is a schematic sectional representation of the third variant for the single-use device in a section along the section line XIII-XIII in FIG. 12.
Figure 14:
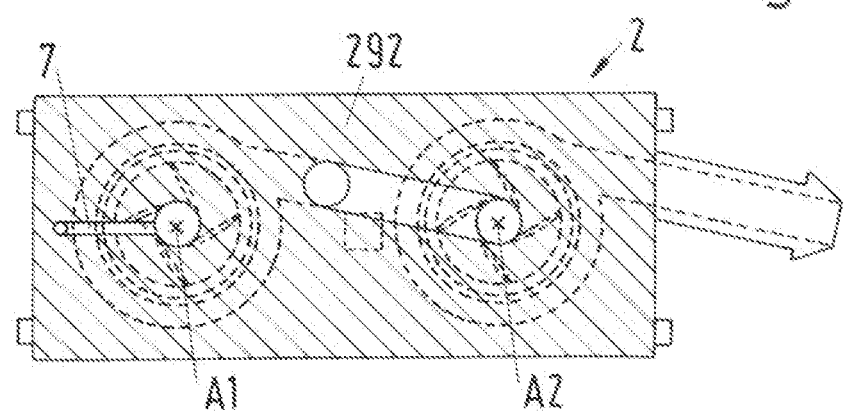
FIG. 14 is a schematic sectional representation of the third variant for the single-use device in a section along the section line XIV-XIV in FIG. 12.

FIG. 10 shows in a representation analogous to FIG. 1 a schematic sectional representation of the fourth embodiment of a pumping device 1 according to the invention in a section along the section line X-X in FIG. 11. FIG. 11 shows in a representation analogous to FIG. 6 a schematic sectional representation of the fourth embodiment of the pumping device 1 according to the invention in a section along the section line XI-XI in FIG. 10. FIG. 12 shows in a representation analogous to FIG. 7 a schematic sectional representation of the third variant for the single-use device 2 in a section along the section line XII-XII in FIG. 13. FIG. 13 shows a schematic sectional representation of the third variant for the single-use device 2 in a section along section line XIII-XIII in FIG. 12, and FIG. 14 shows a schematic sectional representation of the third variant for the single-use device 2 in a section along section the line XIV-XIV in FIG. 12.

In the fourth embodiment of the pumping device 1 according to the invention, the reusable device 3—in an analogous manner to the third embodiment—is designed in such a way that the rotors 214, 224 of the single-use device 2 each rotate about the axes of rotation A1, A2 in the operating state, wherein the axes of rotation A1 and A2 enclose with the vertical an angle different from zero, which is smaller than 90°. This means that the two rotation axes A1 and A2 are inclined to the vertical at an angle different from zero and 90° in the operating state.

The single-use device 2 is designed according to a third variant, in which the flow of the fluid in the single-use device 2 is analogous to that of the second variant of the single-use device 2. Of course, it is also possible that the third variant of the single-use device 2 is designed in the analogously same manner in such a way that the flow of the fluid takes place in a manner analogous to the first variant, namely in such a way that the fluid is only deflected by 90° with respect to the axial direction A between the first outlet 212 and the second inlet 221.

In the third variant, the single-use device 2 comprises three parts 291, 292, 293, each of which is produced separately and then joined together in a joining process. The three parts 291, 292, 293 are designed such that their respective boundary surfaces are aligned perpendicular to the axial direction A. The first part 291 comprises the two protuberances 217, 227, with which the single-use device 2 can be inserted into the reusable device 3. The second part 292 comprises that area which, with respect to the axial direction A, is adjacent to the first part 291 and delimits upwards those cavities in which the two rotors 214 and 224 are arranged. Here, "above" or "upwards" refers to the representation in FIG. 12. The third part 293 forms that area, which delimits the single-use device 2 on its side facing away from the reusable device 3 with respect to the axial direction A and comprises the first inlet 211 and parts of the connecting channel 23.

This embodiment is particularly advantageous from a manufacturing point of view. Each of the parts 291, 292, 293 can be manufactured in a simple way, preferably by an injection molding process, and subsequently the three parts 291, 292, 293 are firmly joined together.

In FIG. 13 and FIG. 14, the first part 291 and the second part 292 are represented. In these sectional representations, the section is made perpendicular to the axial direction in the boundary surface between the first part 291 and the second part 292 (FIG. 13) or in the boundary surface between the second part 292 and the third part 293 (FIG. 14). The position of the sections is represented in FIG. 12. This means that FIG. 13 shows a plan view on the first part 291 and FIG. 14 a plan view on the second part 292, each from the axial direction A.

As already mentioned, each of the three parts 291, 292, 293 is preferably an injection molded part. To manufacture the single-use device 2, the following procedure is preferred: The three parts 291, 292, 293 are manufactured from a plastic by an injection molding process. Subsequently, a rotor 214 or 224 is inserted into the two protuberances 217, 227 of the first part 291 in each case. Then, the second part 292 is placed on the first part 291 and is firmly and sealingly connected to the first part 291 in a joining process. This joining process can, for example, be a bonding process, e.g. a bonding by an adhesive that can be cured with ultraviolet radiation. Furthermore, the joining process can be a welding process, e.g. infrared welding or laser welding or ultrasonic welding. The third part 293 is connected with the second part 292 in the analogously same way. In this variant, the connection channel 23 and the pump housings 213, 223 are thus each formed by cavities which are provided in the three parts 291, 292, 293. Of course, it is also possible to first place all parts 291, 292, 293 on top of each other and only then to firmly connect the three parts 291, 292, 293 with a welding or bonding process.

As can be seen in particular in FIG. 12, a measuring channel 7 or also several measuring channels can be disposed in the single-use device 2, extending from an outside of the single-use device 2 to one of the two inlets 211, 221 or to one of the outlets 212, 222. A sensor (not represented) can be arranged in such a measuring channel with which an operating parameter, e.g. a pressure or the flow through the pumping device 1 can be determined.

In the fourth embodiment of the pumping device 1 according to the invention, a superordinate control unit (electronic controller) 40 (FIG. 10) is further disposed in the stator housing 35. Of course, such a superordinate control unit 40 can also be provided in the previously described embodiments.

This superordinate control unit 40 is signal-connected to the first control device 41 via a first connection 401 and signal-connected to the second control device 42 via a second signal connection 402, so that the superordinate control unit 40 can exchange signals or information with both control devices 41, 42.

Furthermore, the single-use device 2 comprises an identification element 81, with which the single-use device 2 can identify itself on the reusable device 3. The identification element 81 contains specific data, in particular for the single-use device 2, for example calibration data, so that the single-use device 2 can be identified by the reusable device 3 and specific properties of the respective single-use device 2 can be transmitted to the reusable device 3.

For this purpose, the reusable device 3 preferably comprises a recognition element 82, which is designed in such a way that it enables an identification of the respective single-use device 2 or its properties via an interaction with the identification element 81.

Preferably, both the identification element 81 and the recognition element 82 are each designed as an RFID (radio-frequency identification) element. In other embodiments, the identification element 81 and/or the recognition element 82 can comprise a bar code, in particular a two-dimensional or three-dimensional bar code.

The recognition element 82 is signal-connected to the superordinate control unit 40 via an identification connection, so that the superordinate control unit 40 can receive specific data in each case, for example calibration data, from the single-use device 2 inserted in the reusable device 3 and/or can transmit data to this single-use device 2.

Furthermore, two pressure sensors 621 and 622 are provided, wherein the first pressure sensor 621 is arranged such that it can be used to determine the pressure of the fluid at the first inlet 211 and the second pressure sensor 622 is arranged such that it can be used to determine the pressure at the second outlet 222. Thus, the pressure difference generated by the pumping device 1 can be determined by the two pressure sensors 621 and 622.

The two pressure sensors 621 and 622 are signal-connected to the superordinate control unit 40 via the connections 611 and 612. In addition, or if no superordinate control unit 40 is provided, the pressure sensors 621 and 622 can be signal-connected to any of the control devices 41 and 42. This is represented in FIG. 10 only for the pressure sensor 622 at the second outlet 222 with the dashed connections 623 and 624.

The third part 293 can have a projection 294 at its end facing the second part 292 or several projections 294, for example one at each corner, which are designed to interact with retaining elements 394 on the surface of the stator housing 35 (see FIG. 11). Preferably, the projections 294 on the single-use device 2 interact with the retaining elements 394 on the reusable device 3 in the form of snap connections, which prevent an unintentional separation of the single-use device 2 and the reusable device 3.

In the following, the method according to the invention for operating a pumping device 1 according to the invention is now discussed in more detail. In this respect, the pumping device 1 can be designed according to any of the preceding embodiments or variants.

In the method according to an embodiment of the invention, a desired value for an operating parameter of the pumping device 1 is predetermined for each control device 41, 42. An actual value for this operating parameter is determined by a sensor and the actual value is transmitted to each control device 41, 42.

Figure 15:
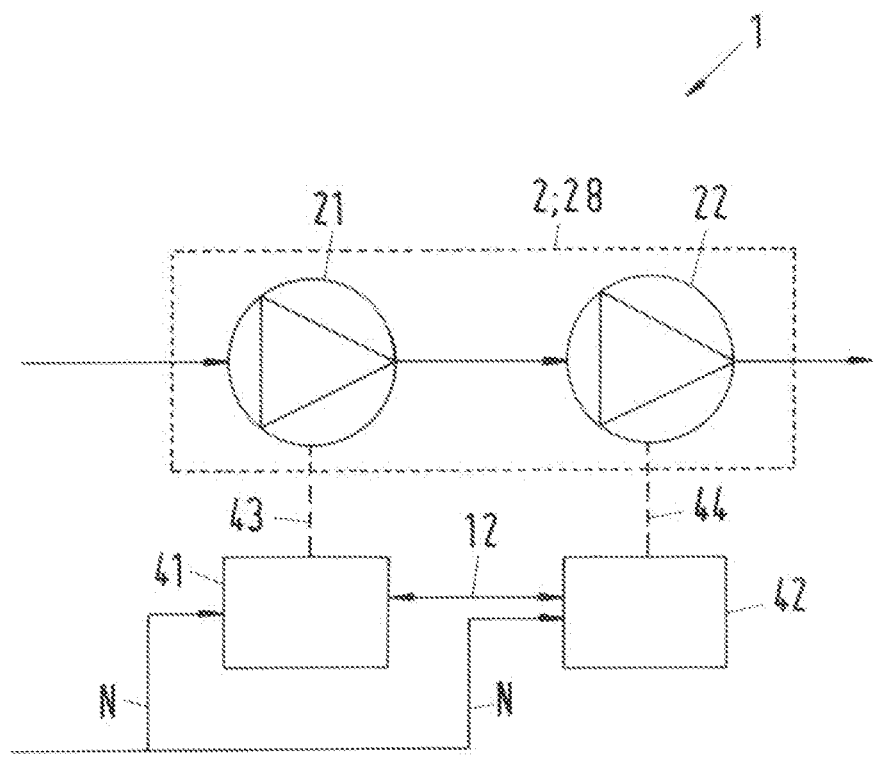
FIG. 15 is a symbolic representation of an embodiment of a pumping device according to the invention to explain an embodiment of a method according to the invention for operating a pumping device according to the invention.

FIG. 15 shows in a symbolic representation an embodiment of the pumping device 1 according to the invention with the two pump units 21, 22, with the two control devices 41, 42 and with the communication connection 12 between the two control devices 41, 42. Furthermore, a first connection 43 and a second connection 44 are represented symbolically in dashed lines. The first connection 43 represents the communication of the first control device 41 with the first pump unit 21 and the second connection represents the communication of the second control device 42 with the second pump unit 22.

In principle, the method according to the invention is based on the fact that for a predetermined pressure difference, which is to be generated by the pumping device 1, the two pump units 21, 22 connected in series are used in normal, i.e. trouble-free operation. In doing so, the rotational speed for each of the two pump units 21, 22 can be reduced by a factor $(1/\sqrt{2})$—compared to the situation when only one pump unit 21 or 22 is used to generate the same pressure difference. This reduction of the rotational speed results in a considerable reduction of the shear forces acting on the fluid to be pumped in the pump units 21, 22. This is an enormous advantage, in particular when conveying biological substances that comprise cells or other sensitive substances, such as blood.

If now, for whatever reason, one of the two pump units 21, 22 or the control devices 41, 42 fails, the rotational speed of the other pump unit 22 or 21 is increased by a factor $\sqrt{2}$, so that the desired pressure difference is now only generated by the one remaining pump unit 22 or 21. This possibility of hot redundant design is a great advantage in particular for medical applications, e.g. pumping blood, or for biotechnological applications, e.g. cell cultivation.

In FIG. 15, the arrows with the reference sign N represent the desired value for the rotational speed of the pump units 21, 22. This desired value N is transmitted to both control devices 41, 42. Via the connection 43 or 44 with its assigned pump unit 21 or 22, each control device 41, 42 receives the actual value for the current rotational speed of the motor with which the respective electromagnetic rotary drive rotates. This rotational speed is determined in a bearingless motor, for example by means of Hall sensors.

The arrows without reference signs on the pump units 21, 22 symbolize the fluid to be conveyed.

Via the communication connection 12, the two control devices 41, 42 can exchange control signals with each other and in particular also exchange the respective actual values for the rotational speed of the motor. As an option (not shown in FIG. 15), additional signal connections can be provided via which the first control device 41 receives directly—i.e. not via the second control device 42—the actual value of the rotational speed of the motor of the second pump unit 22 and the second control device 42 receives directly—i.e. not via the first control device 41—the actual value of the rotational speed of the motor of the first pump unit 21.

Figure 16:
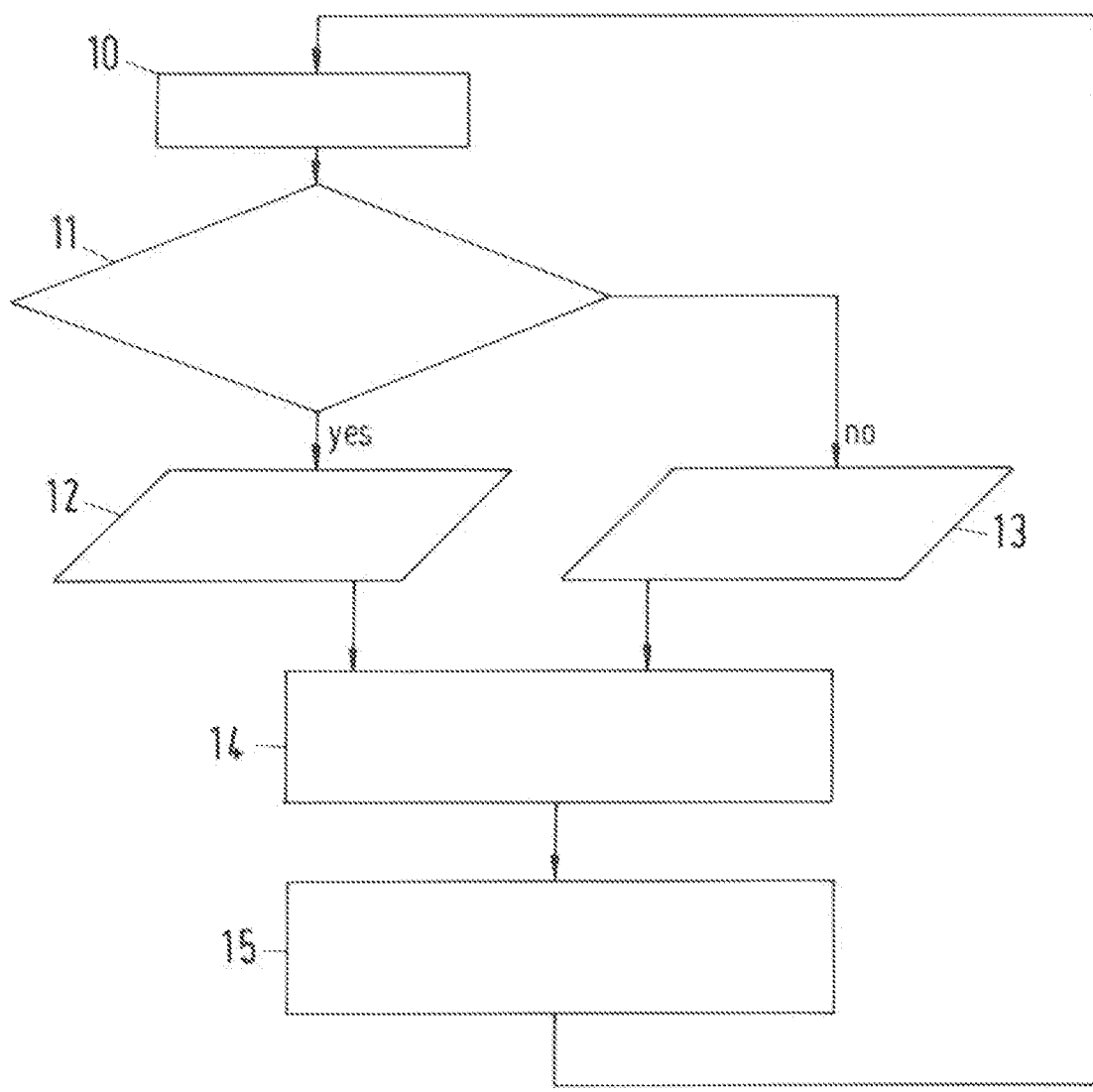
FIG. 16 is a flow chart for the embodiment of the method according to the invention.

The previously described basic embodiment is illustrated in the flow chart in FIG. 16. In step 10, each control device 41, 42 reads in the desired value for the rotational speed of the pump, i.e. the desired value for the rotational speed of the pumping device 1.

In step 11, the two control devices 41 and 42 communicate with each other via communication connection 12 in order to determine whether the bearingless motor of the respective other pump unit 21 or 22 is operating without fault. For such checks, many error detection procedures are known to the person skilled in the art.

If it is determined in step 11 that the bearingless motors of both pump units 21, 22 operate without fault, then in step 12 the actual value for the rotational speed of the motor for both pump units 21, 22 is set to a value which is smaller by a factor $(1/\sqrt{2})$ than the desired value for the rotational speed of the pump.

If it is determined in step 11 that one of the two bearingless motors of the two pump units 21, 22 does nor operate, in step 13 the desired value for the rotational speed of the motor for the other bearingless motor is set to the value for the rotational speed of the pump.

In step 14, it is then checked after step 12 or after step 13 whether the difference between the actual value and the desired value for the rotational speed of the motor is within a predeterminable tolerance range.

In step 15, the two control devices 41 and 42 then exchange the result of the check in step 14 via the communication connection 12.

The procedure then starts again at step 10.

In order to ensure a particularly high operational reliability, preferably all connections via which information is exchanged, i.e. for example the communication connection 12, are designed redundantly.

Figure 17:
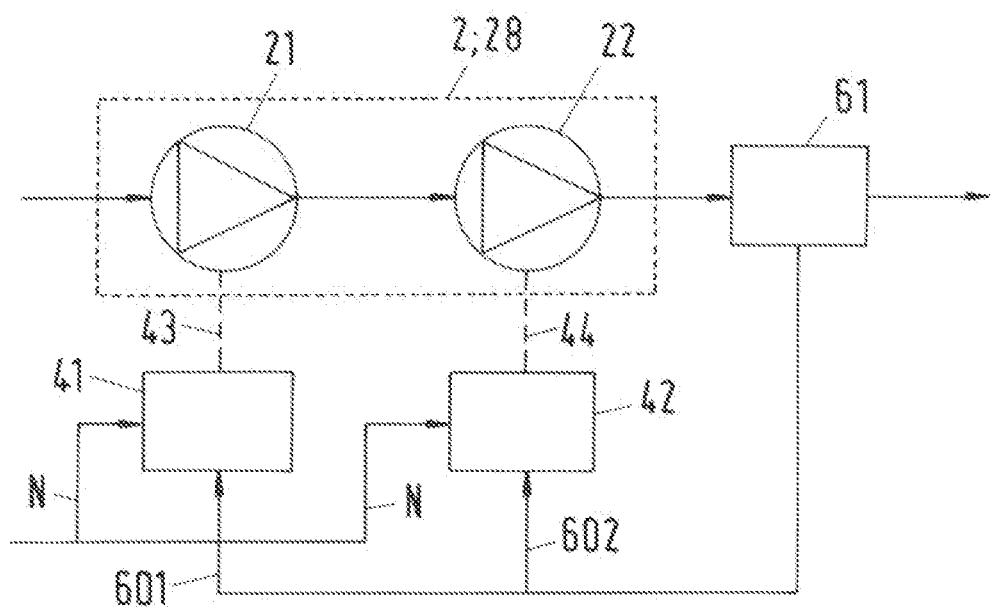
FIGS. 17-20 are different variants for the embodiment of the method according to the invention, each in a representation analogous to FIG. 15.

FIG. 17 shows a first variant for the embodiment of the method according to the invention in a symbolic representation analogous to FIG. 15. In this first variant, the flow through the pumping device 1 is used as an operating parameter. For this purpose, the flow sensor 61 is provided which is preferably arranged near the second outlet 222. As already mentioned above, the flow sensor 61 is signal-connected to the first control device 41 via the first signal connection 601 and to the second control device 42 via the second signal connection 602. Thus, the flow sensor 61 can lead the actual value of the flow to the two control devices 41, 42, which then compare this actual value with the desired value for the flow and regulate the actual value of the flow to the desired value in case of discrepancies. For this regulation, the communication connection 12 between the two control devices 41, 42 is not absolutely necessary. If one of the control devices 41 or 42 or one of the pump units 21 or 22 fails, this leads to a change in the actual value for the flow, which is communicated to both control devices 41, 42 via the signal connections 601, 602. The still functioning control device 41 or 42 or the control device 41, 42 of the still functioning pump unit 21 or 22 will then change the rotational speed of the associated bearingless motor in such a way that the actual value of the flow is brought back to the desired value of the flow.

Figure 18:
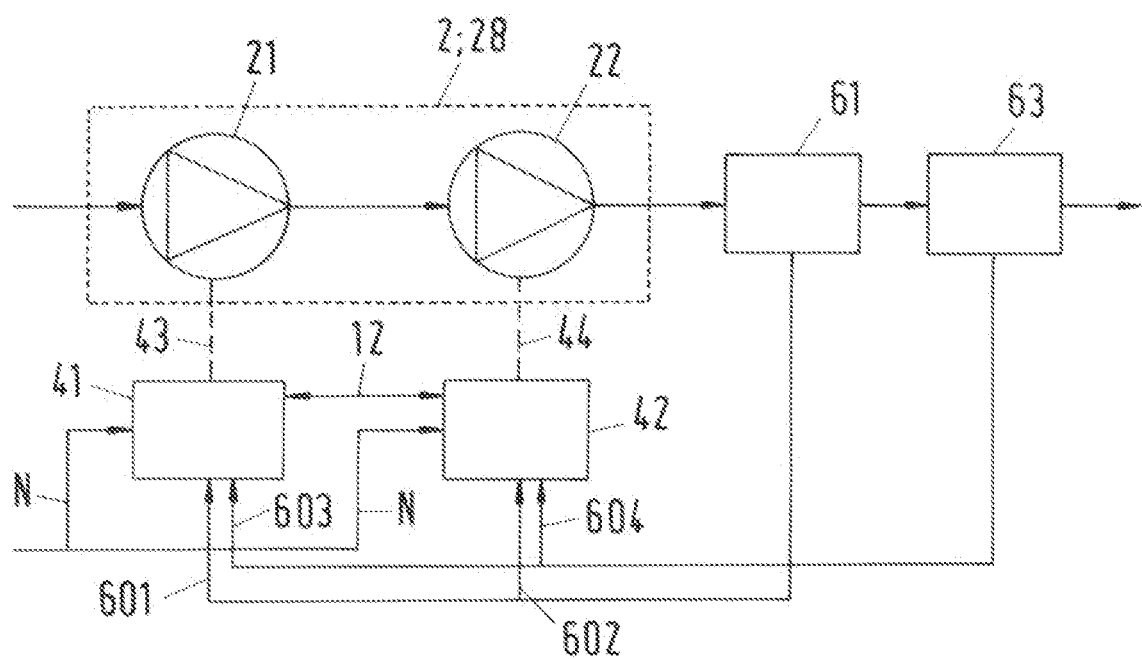

FIG. 18 shows a second variant for the embodiment of the method according to the invention in a symbolic representation analogous to FIG. 15. In this second variant, the flow through the pumping device 1 is also used as the operating parameter. In contrast to the first variant, in the second variant the flow measurement for determining the actual value of the flow is designed redundantly. As shown in FIG. 18, for example, this can be realized in such a way that a second flow sensor 63 is provided in addition to the flow sensor 61. Then, each flow sensor 61, 63 is signal-connected to each control device 41, 42. The flow sensor 61 is signal-connected to the first control device 41 or to the second control device 42 via the signal connections 601, 602, and the second flow sensor 63 is signal-connected to the first control device 41 or to the second control device 42 via signal connections 603 and 604. As an alternative, it is of course also possible to provide only one flow sensor instead of two flow sensors 61, 63, which is designed redundantly in such a way, for example by the number of ultrasonic transducers, that it enables two independent measurements of the flow.

Figure 19:
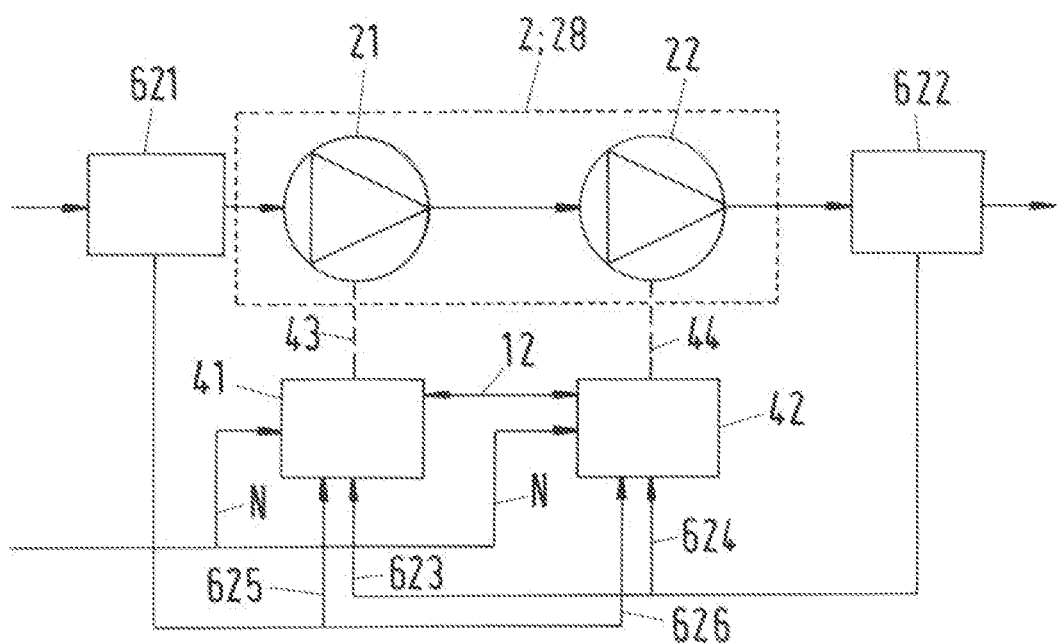

FIG. 19 shows a third variant for the embodiment of the method according to the invention in a symbolic representation analogous to FIG. 15. In this third variant, the pressure difference generated by the pumping device 1 is used as operating parameter. For this purpose, two pressure sensors 621 and 622 are provided (see also FIG. 10) wherein the first pressure sensor 621 is arranged such that the pressure of the fluid at the first inlet 211 can be determined with it and the second pressure sensor 622 is arranged such that the pressure at the second outlet 222 can be determined with it. By the two pressure sensors 621 and 622, the pressure difference generated by the pumping device 1 can thus be determined. Each of the two pressure sensors 621 and 622 is signal-connected in each case to both control devices 41 and 42. The pressure sensor 622 is signal-connected to the first control device 41 or to the second control device 42 via the connections 623 or 624. The pressure sensor 621 is signal-connected to the first control device 41 or to the second control device 42 via the connections 625 or 626.

Thus, the two pressure sensors 621 and 622 can transmit the actual value of the pressure at the first inlet 211 and the actual value of the pressure at the second outlet 222 to both control devices 41, 42 in each case. The control devices 41, 42 then determine the actual value for the pressure difference generated by the pumping device 1 and compare it with the desired value for the pressure difference. In the case of discrepancies between the actual value and the desired value for the pressure difference, which exceed a predeterminable tolerance range, the actual value of the pressure difference is regulated to the desired value. For this regulation, the communication connection 12 between the two control devices 41, 42 is not absolutely necessary. If one of the control devices 41 or 42 or one of the pump units 21 or 22 fails, this leads to a change in the actual value for the pressure difference, which can be detected by both control devices 41, 42. The still functioning control device 41 or 42 or the control device 41, 42 of the still functioning pump unit 21 or 22 will then change the rotational speed of the associated bearingless motor in such a way that the actual value of the pressure difference is brought back to the desired value of the pressure difference.

Figure 20:
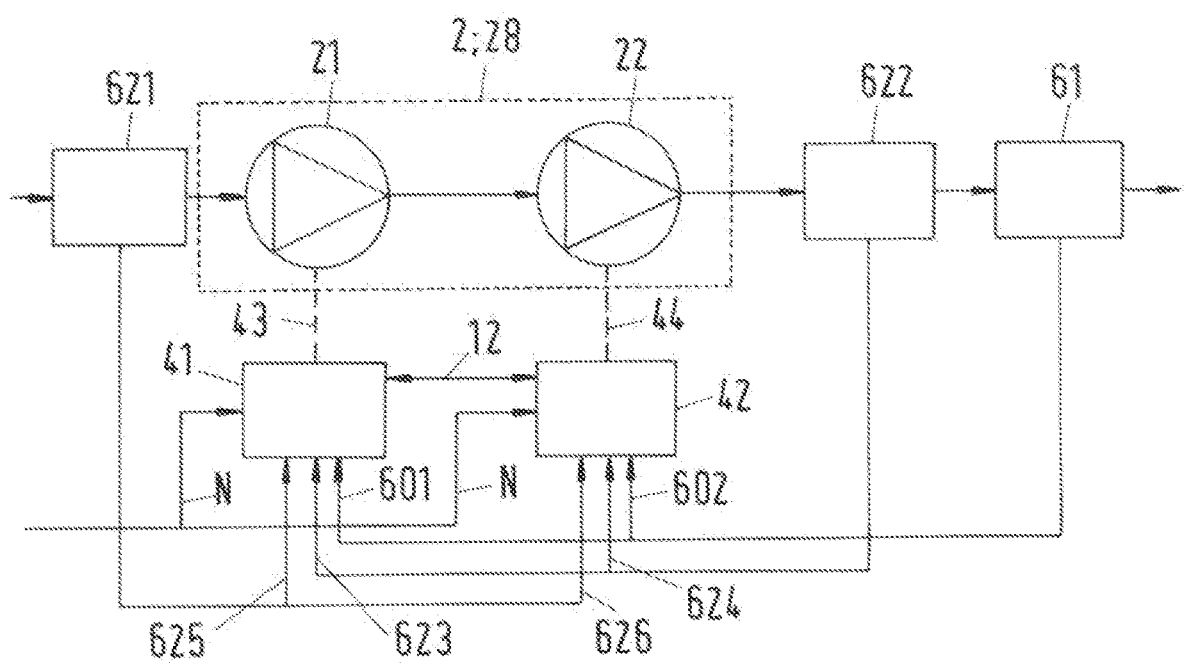

FIG. 20 shows a fourth variant for an embodiment of the method according to the invention in a symbolic representation analogous to FIG. 15. In this fourth variant, two operating parameters are used, namely the pressure difference generated by the pumping device 1 and the flow through the pumping device 1. Thus, this fourth variant is a combination of the third variant (FIG. 19) with the second variant (FIG. 18) or with the first variant (FIG. 17). In the fourth variant, therefore, both the pressure sensors 621 and 622 are provided, with which the pressure difference generated by the pumping device 1 can be determined, and the flow sensor 61, with which the flow through the pumping device 1 can be determined. In this embodiment, it is possible that only one flow sensor 61 is provided, as explained in FIG. 17, or that two flow sensors 61, 63 (see FIG. 18) are provided or a redundantly designed flow sensor 61.

In particular with regard to the operating parameters pressure difference and flow, it is also possible that these operating parameters are determined alternatively or additionally from other operating parameters of the pumping device 1.

For example, the flow through the pumping device 1 can be determined from the rotational speed of the bearingless motor and the generated torque. The torque of a bearingless motor is known very precisely from the electrical values, because with a bearingless motor there is no friction as for example with mechanical bearings.

Then, the torque for different rotational speeds can be represented as a function that depends on the density of the fluid, its viscosity (dynamic viscosity) and the flow. Using a reference fluid, for example human or animal blood at a temperature of 37° C., a family of characteristic curves can then be recorded experimentally for different rotational speeds, which shows the dependence of the flow on the torque. As already mentioned, this family of characteristic curves can then be depicted by a family of functions in order to determine the coefficients for the parameters in the functional correlation in this way. These parameters or the functional correlation can then be stored in the control devices 41, 42, so that during operation the actual value of the flow can be determined from the actual value of the torque.

As an alternative, it is of course also possible to store the entire family of characteristic curves, for example as a look-up table in the two control devices 41, 42.

Depending on which values are known from the family of characteristic curves "torque-flow", it is also possible to determine other values of the fluid. In the family of characteristic curves "torque-flow", for example, the torque at zero flow is proportional to the viscosity. This means, for example, that if the flow is determined by measurement, the viscosity of the fluid can be determined. In this way, for example, it is also possible to generate a family of characteristic curves "torque-flow" in which the viscosity is the parameter, i.e. the different curves of the characteristic diagram belong to different viscosities.

The pumping device 1 according to the invention or the method according to the invention are particularly suitable for applications in which very sensitive substances such as blood or biotechnological fluids containing cells, proteins or other sensitive ingredients are conveyed. With an exemplary character are mentioned here: Extracorporeal membrane oxidation (ECMO) for the support of the lung function, applications in heart-lung machines, biopharmaceutical production processes, for example filtration processes in which the desired substances (for example proteins) are removed as permeate from a fluid which is produced in a bioreactor, perfusion processes in the biotechnological or biopharmaceutical industry.

In the previous description, pumping devices 1 are explained, which have two pump units 21, 22. However, such embodiments of the pumping device according to the invention are also possible in which more than two pump units, for example three or even more pump units are connected in series one behind the other.

What is claimed:
1. A pumping device for conveying a fluid, comprising:
a single-use device designed for single use;
a reusable device designed for multiple use,
the single-use device configured to be inserted into the reusable device and comprising two pump units arranged in series one behind the other, each pump unit of the two pump units comprising a rotor configured to convey the fluid, each rotor of the two pump units being a rotor of a bearingless motor, and capable of being magnetically levitated without contact and driven without contact for rotation about an axial direction, the reusable device configured to receive the single-use device and comprising, for each rotor of the two pump units, a stator which forms with a respective rotor an electromagnetic rotary drive configured to rotate the respective rotor about the axial direction, each stator being a bearing and drive stator with which the respective rotor is capable of being magnetically driven without contact and capable of being magnetically levitated without contact with respect to the stator; and an independent controller for each stator, which is configured to independently activate a respective stator.

2. The pumping device according to claim 1, wherein the single-use device has two cup-shaped protuberances in each of which one of the rotors of the two pump units is disposed, and the reusable device has two recesses, each of which is configured to receive one of the two cup-shaped protuberances.

3. The pumping device according to claim 2, wherein the reusable device is configured such that, in an operating state, the rotors of the two pump units of the single-use device each rotate about a respective axis of rotation which encloses with a vertical an angle different from zero, and which is less than 90°.

4. The pumping device according to claim 1, wherein the two pump units includes a first pump unit and a second pump unit, the first pump unit having a first inlet and a first outlet for the fluid, the second pump unit having a second inlet and a second outlet for the fluid, each inlet of the first and second inlets is configured such that the fluid flows to a respective rotor from the axial direction, and each of the first and second outlets is configured such that the fluid leaves a respective pump unit in a discharge direction which is aligned perpendicular to the axial direction.

5. The pumping device according to claim 4, wherein the pumping device is configured such that the fluid is diverted between the first outlet and the second inlet by at least 90°.

6. The pumping device according to claim 4, wherein the pumping device is configured such that the fluid is diverted between the first outlet and the second inlet by a total of 270°.

7. The pumping device according to claim 1, wherein a separate power supply is provided for each of the stators, so that each of the stators is capable being separately supplied with power.

8. The pumping device according to claim 1, further comprising a superordinate controller signal-connected to each of the independent controllers for the stators.

9. The pumping device according claim 1, further comprising an emergency energy store from which energy is capable of being supplied to each stator when a primary energy source configured to supply energy to the stators is no longer capable of providing energy to least one of the two pump units.

10. The pumping device according to claim 1, wherein the single-use device or the reusable device includes an identification element with which the single-use device and the reusable device are capable of exchanging information with each another.

11. A single-use device designed for single use with a pumping device, and configured to be inserted into a reusable device, the single-use device comprising: two pump units arranged in series one behind the other, each pump unit of the two pump units comprising a rotor configured to convey a fluid, each rotor of the rotors of the two pump units being a rotor of a bearingless motor capable of being magnetically levitated without contact and driven without contact for rotation about an axial direction, and configured to form an electromagnetic rotary drive with a respective stator of the reusable device to rotate the respective rotor about the axial direction, each stator being a bearing and drive stator with which the respective rotor is capable of being magnetically driven without contact and capable of being magnetically levitated without contact with respect to the stator.

12. A method for operating the pumping device according to claim 1, the method comprising:
   setting a predetermined desired value for an operating parameter of the pumping device for each independent control device;
   determining, with a sensor, an actual value for the operating parameter; and
   transmitting the actual value to each independent control device.

13. The method according to claim 12, further comprising exchanging signals between the independent control devices so that independent control device of one of the two pump units determines a functioning of the other of the two pump units.

14. The method according to claim 12, wherein the operating parameter is a flow through the pumping device or a pressure difference generated by the pumping device.

15. The method according to claim 12, further comprising determining a flow through the pumping device from a rotational speed and a torque with which the rotors of the two pump units are driven.

* * * * *